United States Patent
Orban et al.

(10) Patent No.: US 10,716,836 B2
(45) Date of Patent: Jul. 21, 2020

(54) METHODS FOR TREATING AUTOIMMUNE DISEASE BY INDUCING AUTOANTIGEN-SPECIFIC REGULATORY CD4+ T CELLS

(75) Inventors: Tihamer Orban, Brookline, MA (US); Peter Blackburn, New York, NY (US)

(73) Assignees: Joslin Diabetes Center Inc., Boston, MA (US); Mercia Pharma, Inc., New York, NY (US)

( * ) Notice: Subject to any disclaimer, the term of this patent is extended or adjusted under 35 U.S.C. 154(b) by 1555 days.

(21) Appl. No.: 12/290,049

(22) Filed: Oct. 27, 2008

(65) Prior Publication Data

US 2009/0142308 A1    Jun. 4, 2009

Related U.S. Application Data

(63) Continuation-in-part of application No. PCT/US2007/067396, filed on Apr. 25, 2007.

(60) Provisional application No. 60/794,802, filed on Apr. 25, 2006.

(51) Int. Cl.
    *A61K 39/00*     (2006.01)
    *C12N 5/0783*    (2010.01)

(52) U.S. Cl.
    CPC ........ *A61K 39/0008* (2013.01); *C12N 5/0636* (2013.01); *A61K 2039/515* (2013.01)

(58) Field of Classification Search
    CPC .......... A61K 39/0008; A61K 2039/515; C12N 5/0636; A61P 3/10
    See application file for complete search history.

(56) References Cited

U.S. PATENT DOCUMENTS

| | | | |
|---|---|---|---|
| 4,281,061 A | 7/1981 | Zuk et al. | |
| 4,317,811 A | 3/1982 | Bertland et al. | |
| 5,075,110 A | 12/1991 | Francon et al. | |
| 5,447,843 A | 9/1995 | McGuire et al. | |
| 5,645,998 A | 7/1997 | Atkinson et al. | |
| 5,656,289 A * | 8/1997 | Cho et al. | 424/455 |
| 5,759,551 A | 6/1998 | Ladd et al. | |
| 5,891,435 A * | 4/1999 | Muir et al. | 424/185.1 |
| 5,895,653 A * | 4/1999 | Eibl et al. | 424/204.1 |
| 5,998,366 A | 12/1999 | Tobin et al. | |
| 6,110,746 A | 8/2000 | Cohen et al. | |
| 6,462,185 B1 | 10/2002 | Takakura et al. | |
| 7,241,448 B2 | 7/2007 | Jackson et al. | |
| 2003/0045467 A1 | 3/2003 | Orban | |
| 2005/0186207 A1* | 8/2005 | Bluestone et al. | 424/144.1 |
| 2006/0063256 A1 | 3/2006 | Norment et al. | |
| 2006/0183670 A1 | 8/2006 | Orban | |
| 2007/0225210 A1* | 9/2007 | Blackburn | 514/3 |

FOREIGN PATENT DOCUMENTS

| | | |
|---|---|---|
| WO | WO 2004/110373 | 12/2004 |
| WO | 2005070090 A2 | 8/2005 |
| WO | 2007117602 A2 | 10/2007 |
| WO | 2007125362 A1 | 11/2007 |
| WO | 2007127787 A2 | 11/2007 |
| WO | 2007136518 A2 | 11/2007 |
| WO | 2008092905 A2 | 8/2008 |
| WO | 2009003185 A1 | 12/2008 |

OTHER PUBLICATIONS

Sakaguchi. Naturally arising Foxp3-expressing CD25+CD4+ regulatory T cells in immunological tolerance to self and non-self. Nature Immunology. Apr. 2005, vol. 6 Issue 4, p. 345-352.*
Hong et al. Induction of CD4_CD25_ regulatory T cells by copolymer-I through activation of transcription factor Foxp3. 2005. PNAS vol. 102, No. 18; p. 6449-6454.*
Monti et al. Evidence for in Vivo Primed and Expanded Autoreactive T Cells as a Specific Feature of Patients with Type 1 Diabetes. The Journal of Immunology, 2007, 179: 5785-5792.*
Pinkse et al. Autoreactive CD8 T cells associated with B cell destruction in type 1 diabetes. PNAS 2005. vol. 102. No. 51: p. 18425-18430.*
Trudeau et al. Prediction of spontaneous autoimmune diabetes in NOD mice by quantification of autoreactive T cells in peripheral blood. J. Clin. Invest. 111:217-223 (2003).*
Yoon et al. Autoimmune Destruction of Pancreatic b Cells. American Journal of Therapeutics 12, 580-591 (2005).*
Roep, B. O. 1999. Standardization of T-cell assays in type I diabetes. Immunology of Diabetes Society T-Cell Committee. Diabetologia 42: 636-637.*
Orban, T., et al., Autoantigen-specific regulatory T cells induced in patients with Type 1 Diabetes Mellitus by Insulin B-chain immunotherapy, J. Autoimmun. vol. 34(4), 408-415 (2010).
Brusko, T., et al., Treg in type 1 diabetes, Cell Biochem Biophys., vol. 48, 65-175, 2007.
Dejaco, C., et al., Imbalance of regulatory T cells in human autoimmune diseases, Immunology, vol. 117, 289-300, 2005.
Chen, Z., et al., Where CD4+CD25+ T reg cells impinge on autoimmune diabetes, Journal of Experimental Medicince, vol. 202, No. 10, 1387-1397, 2005.

(Continued)

*Primary Examiner* — Taeyoon Kim
(74) *Attorney, Agent, or Firm* — Pierce Atwood LLP; Kevin M. Farrell

(57) ABSTRACT

Described herein are methods and compositions for the treatment and monitoring the progress of autoimmune diseases. In some embodiments, the methods include the stimulation of regulatory T cells specific to autoantigens associated with the autoimmune disease. A specific embodiment relates to diabetes mellitus, and the prevention or delay of loss of residual β-cell mass, providing a longer remission period and delaying the onset of diabetes related, progressive, complications through immunotherapeutic induction of regulatory T cells specific for human insulin B chain. In addition, the methods described herein can be used to predict whether a subject, e.g., a subject with ongoing anti-insulin autoimmunity, will progress to T1DM, and to evaluate a subject's response to a therapeutic intervention.

10 Claims, 7 Drawing Sheets

Specification includes a Sequence Listing.

(56) References Cited

OTHER PUBLICATIONS

Rothel, J.S., et al., Urea/DTT solubilization of a recombinant Taenia ovis antigen, 45W, expressed as a GST fusion protein results in enhanced protective immune response to the 45W moiety, Vaccine, vol. 15(5), 469-472, 1997.
Orban, T., IPRP for PCT/US2007/067396, 2007.
Bergerot et al., "Insulin B-chain reactive CD4+ regulatory T-cells induced by oral insulin treatment protect from type 1 diabetes by blocking the cytokine secretion and pancreatic infiltration of diabetogenic effector T-cells," Diabetes, 48(9):1720-1729 (1999).
Argardh et al., "Clinical evidence for the safety of GAD65 immunomodulation in adult-onset autoimmune diabetes", Journal of Diabetes and Its Complications, 19: 238-246 (2005).
Faustman et al., "Immunotherapy of Trial for New-Onset Type 1 Diabetes," The New England Journal of Medicine, 10.1056/NEJMe0807425: 1-4 (2008).
Lernmark, "Type 1 Diabetes—Does Suppressing T Cells Increase Insulin?", The New England Journal of Medicine, 352:2642-2644 (2005).
Lernmark and Agardh, "Immunomodulation with human recombinant autoantigens," Trends in Immunology, 26(11):608-612.
Ludvigsson et al., "GAD Treatment and Insulin Secretion in Recent-Onset Type I Diabetes," The New England Journal of Medicine, 10.1056/NEJMoao804328: 1-12 (2008).
Aanstoot et al., "Identification and characterization of glima 38, a glycosylated islet cell membrane antigen, which together with GAD65 and IA2 marks the early phases of autoimmune response in type 1 diabetes," J. Clin. Invest., 97(12):2772-2783 (1996).
Alcalde et al., "Cloning of candidate autoantigen carboxypeptidase H from a human islet library: sequence identity with human brain CPH," J. Autoimmun., 9(4):525-528 (1996).
Argentaro et al., "Linkage studies of SOX13, the ICA12 autoantigen gene, in families with type 1 diabetes," Molecular Genetics and Metabolism, 72:356-359 (2001).
Aruna et al., "Down-regulation of T cell responses to AChR and reversal of EAMG manifestations in mice by a dual altered peptide ligand via induction of CD4+ CD25+ regulatory cells ," J. Neuroimmunol., 177:63-75 (2006).
Boitard et al., "Peripherin: an islet antigen that is cross-reactive with nonobese diabetic mouse class II gene products," Proc. Natl. Acad. Sci. USA, 89(1):172-176 (1992).
Castano et al., "Identification and cloning of a granule autoantigen (carboxypeptidase-H) associated with type I diabetes," J. Clin. Endocrinol. Metab., 73(6):1197-1201 (1991).
Cox et al., "Adjuvants—a classification and review of their modes of action," Vaccine, 15(3):248-256 (1997).
Dionisi et al., "Target antigens in autoimmune diabetes: pancreatic gangliosides," Ann. 1st Super Sanita, 33(3):433-435 (1997).
Dong et al., "Transplantation tolerance: the concept and its applicability," Ped. Transplant., 3:181-192 (1999).
Dotta et al., "Autoimmunity to the GM2-1 islet ganglioside before and at the onset of type I diabetes," Diabetes, 45(9):1193-1196 (1996).
Durinovic-Bello et al., "Predominantly recognized proinsulin T helper cell epitopes in individuals with and without islet cell autoimmunity," J. Autoimmun., 18:55-66 (2002).
Dzhambazov et al., "Therapeutic vaccination of active arthritis with a glycosylated collagen type II peptide in complex with MHC class II molecules," J. Immunol., 176:1525-1533 (2006).
Elias et al., "Induction of diabetes in standard mice by immunization with the p277 peptide of a 60-kDa heat shock protein," Eur. J. Immunol 25(10):2851-2857 (1995).
Elias et al., "Peptide therapy for diabetes in NOD mice," Lancet, 343(8899):704-706 (1994).
Estuningsih et al., "Evaluation of antigens of Fasciola gigantica as vaccines against tropical fasciolosis in cattle," Int. J. Parasitol., 27(11):1419-1428 (1997).
Fineberg et al., "Immunological responses to exogenous insulin," Endocr. Rev., 28:625-652 (2007).
Goodnow, "Pathways for self-tolerance and the treatment of autoimmune diseases," The Lancet, 357:2115-2121 (2001).
Karges et al., "Induction of Autoimmune Diabetes Through Insulin (but Not GAD65) DNA Vaccination in Nonobese Diabetic and in RIP-B7.1 Mice," Diabetes, 51:3237-3244 (2002).
Karlsen et al., "Cloning and primary structure of a human islet isoform of glutamic acid decarboxylase from chromosome 10," Proc. Natl. Acad .Sci. USA, 88(19):8337-8341 (1991).
Kasimiotis et al., "Sex-determining region Y-related protein SOX13 is a diabetes autoantigen expressed in pancreatic islets," Diabetes, 49(4):555-561 (2000).
Keller et al., "Insulin prophylaxis in individuals at high risk of type I diabetes," Lancet, 341:927-928 (1993).
Kent et al., "Expanded T cells from pancreatic lymph nodes of type 1 diabetic subjects recognize an insulin epitope," Nature, 435:224-228 (2005).
Kukreja et al., "Autoimmunity and Diabetes," J. Clinical Endocrin. & Metab., 84(12):4371-4378 (1999).
Leslie et al., "Autoantigens IA-2 and GAD in type I (insulin-dependent) diabetes," Diabetologia, 42:3-14, (1999).
Mallone et al., "MHC Class II tetramers and the pursuit of antigen-specific T cells: define, deviate, delete," Clin. Immunol., 110:232-242 (2004).
Marketletter, Newsletter, Autoimmune Shares Collapse on Collorol Data in Rheumatoid Arthritis Marketletter Publications Ltd., (Sep. 13, 1999).
Masteller et al., "Expansion of Functional Endogenous Antigen-Specific $CD4^+$ $CD25^+$ Regulatory T Cells from Nonobese Diabetic Mice," The Journal of Immunology, 175:3053-3059 (2005).
Muir et al., "Insulin Immunization of Nonobese Diabetic Mice Induces a Protective Insulitis Characterized by Diminished Intraislet Interferon-gamma Transcription," J. Clin. Invest., 95:628-634 (1995).
Nakayama et al., "Prime role for an insulin epitope in the development of type 1 diabetes in NOD mice," Nature, 435:220-223 (2005).
Orban et al., "Diabetes Insulin Immune Effect Prevents Diabetes in NOD Mice," Diabetes, 48(Supp.1):A216-A217 (1999).
Pietropaolo et al., "Islet Cell Autoantigen 69 kD (ICA69)," J. Clin. Invest., 92:359-371 (1993).
Pozzilli et al., "No effect of oral insulin on residual beta-cell function in recent-onset type I diabetes (the IMDIAB VII). IMDIAB Group," Diabetol., 43:1000-1004 (2000).
Prakken et al. "Heat shock protein 60 and adjuvant arthritis: a model for T cell regulation in human arthritis ," Springer Semin. Immunopathol. 25(1):47-63 (2003).
Quintana et al., "Inhibition of adjuvant arthritis by a DNA vaccine encoding human heat shock protein 60," J. Immunol., 169:3422-3428 (2002).
Rabin et al., "Islet cell antigen 512 is a diabetes-specific islet autoantigen related to protein tyrosine phosphatases," J. Immunol., 152(6):3183-3188 (1994).
Ramiya et al., "Antigen Based Therapies to Prevent Diabetes in NOD Mice," 9:349-356 (1996).
Ramiya et al., "Immunization Therapies in the Prevention of Diabetes," J. Autoimmunity, 10:287-292 (1997).
Seddon et al., "Peripheral Autoantigen Induces Regulatory T Cells that Prevent Autoimmunity," The Journal of Experimental Medicine, 189(5):877-881 (1999).
Shah et al., "A randomized trial of intensive insulin therapy in newly diagnosed insulin-dependent diabetes mellitus," The New England Journal of Medicine, 320:550-554 (1999).
Simone et al., "Immunologic "vaccination" for the prevention of autoimmune diabetes (type 1A)," Diabetes Care, 22:B7-B15 (1999).
Skylar et al., "Effects of oral insulin in relatives of patients with type 1 diabetes: The Diabetes Prevention Trial—Type 1," Diabet. Care, 28(5):1068-1076 (2005).
Tang et al., "In Vitro-Expanded Antigen-specific Regulatory T Cells Suppress Autoimmune Diabetes," The Journal of Experimental Medicine, 199(11):1455-1465 (2004).

(56) References Cited

OTHER PUBLICATIONS

Tarbell et al., "CD25+ CD4+ T Cells, Expanded with Dendritic Cells Presenting a Single Autoantigenic Peptide, Suppress Autoimmune Diabetes," The Journal of Experimental Medicine, 199(11):1467-1477 (2004).

Tiittanen et al., "Insulin Treatment in Patients with Type 1 Diabetes Induces Upregulation of Regulatory T-cell Markers in Peripheral Blood Mononuclear Cells Stimulated with Insulin in Vitro," Diabetes, 55:3446-3454 (2006).

van Roon et al. "Stimulation of suppressive T cell responses by human but not bacterial 60-kD heat-shock protein in synovial fluid of patients with rheumatoid arthritis," J. Clin. Invest. 100:459-163 (1997).

Xie et al., "Autoantibodies to IA-2 and IA-2 beta in insulin-dependent diabetes mellitus recognize conformational epitopes: location of the 37- and 40-kDa fragments determined," J. Immunol., 159:3662-3667 (1997).

Zhang et al., "Autoantibodies to IA-2 in IDDM," Diabetes 46:40-43 (1997).

Bresson, D., et al., Anti-CD3 and nasal proinsulin combination therapy enhances remission from recent-onset autoimmune diabetes by inducing Tregs, The Journal of Clinical Investigation, vol. 116, No. 5, May 2006, 1371-1381.

Homann, D., et al., Regulatory T cells and type 1 diabetes, Clinical Immunology, vol. 112, Mar. 27, 2004, 202-209.

Mukherjee, R., et al., CD4+CD25+ regulatory T cells generated in response to insulin B:9-23 peptide prevent adoptive transfer of diabetes by diabetogenic T cells, Journal of Immunology, vol. 21, May 23, 2003, 221-237.

Bluestone, J., et al., How do CD4+CD25+ regulatory T cells control autoimmunity? Current Opinion in Immunology, vol. 17, Oct. 4, 2005, 638-642.

Gupta, et al. "Adjuvants for human vaccines—current status, problems and future prospects" Vaccine; 1995; vol. 13; No. 14; pp. 1263-1276.

Aguilar, et al. "Vaccine adjuvants revisited" Vaccine; 2007; vol. 25; pp. 3752-3762.

Savelkoul, et al. "Choice and design of adjuvants for parenteral and mucosal vaccines" Vaccines; 2015; vol. 3; pp. 148-171.

Reed, et al. "New horizons in adjuvants for vaccine development" Cell Press; 2008; pp. 23-32.

\* cited by examiner

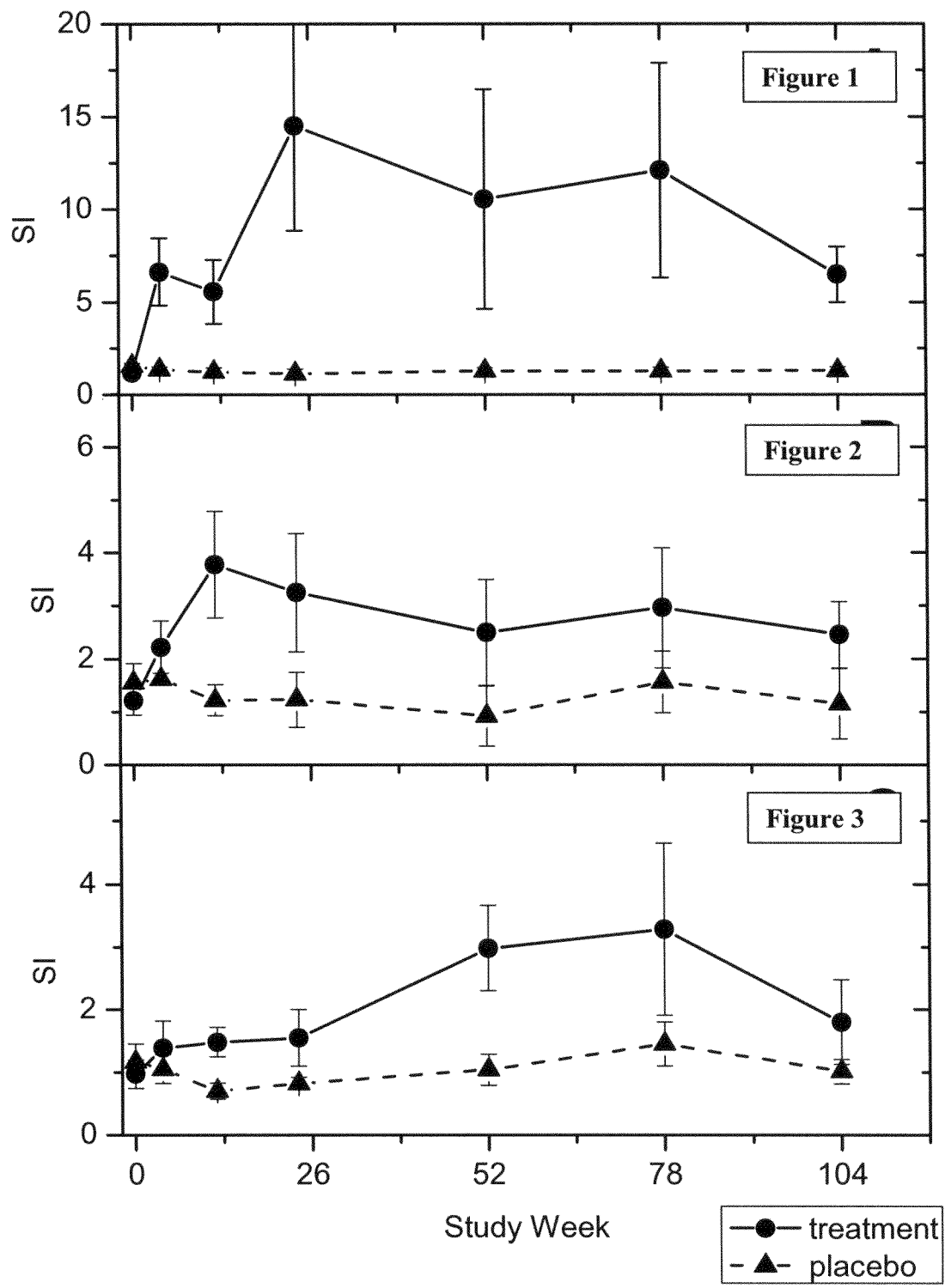

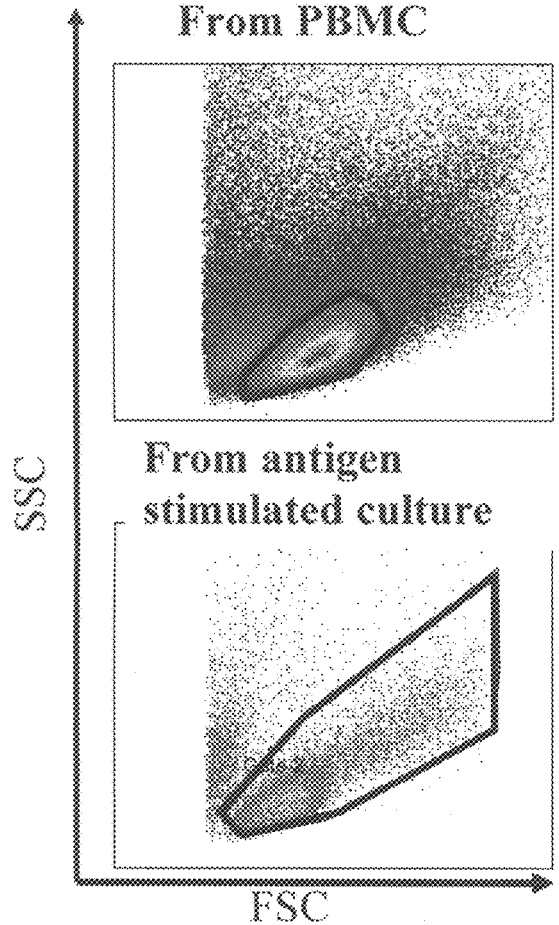
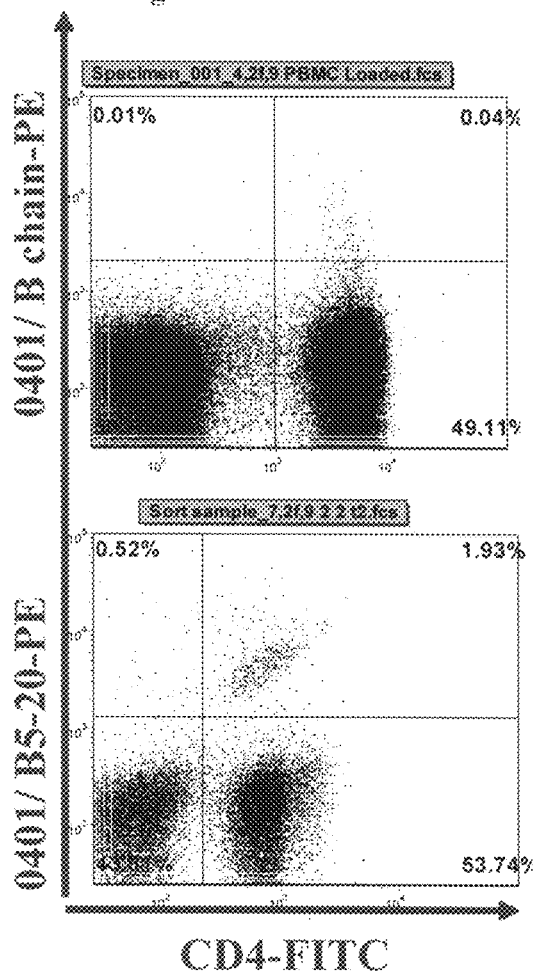

4/9 PBMC and 4/9 B chain stimulated cell culture
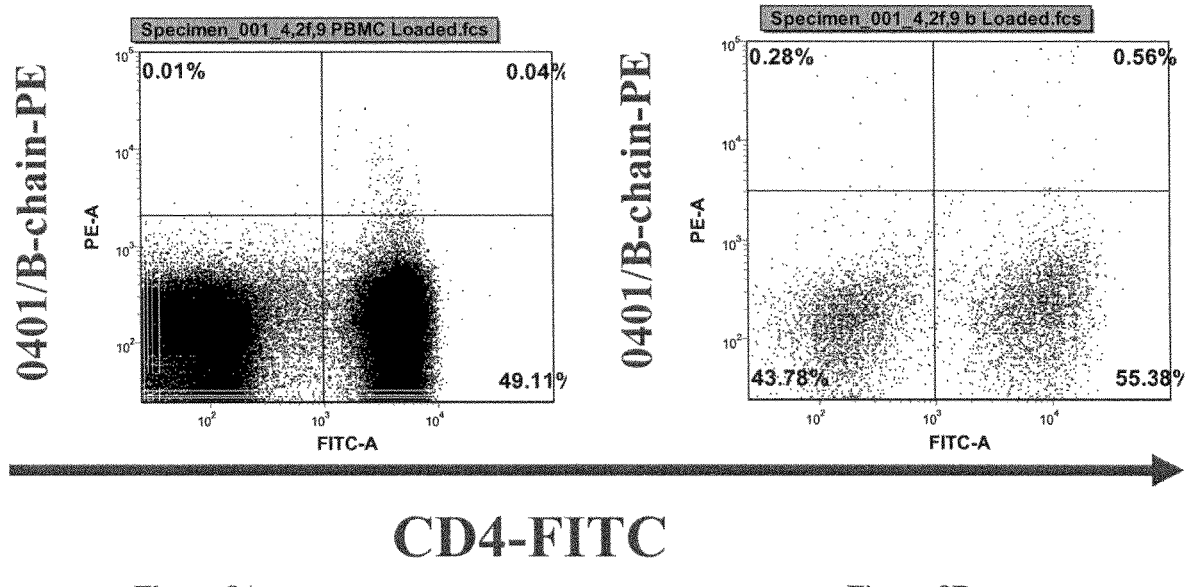
Figure 8A
Figure 8B
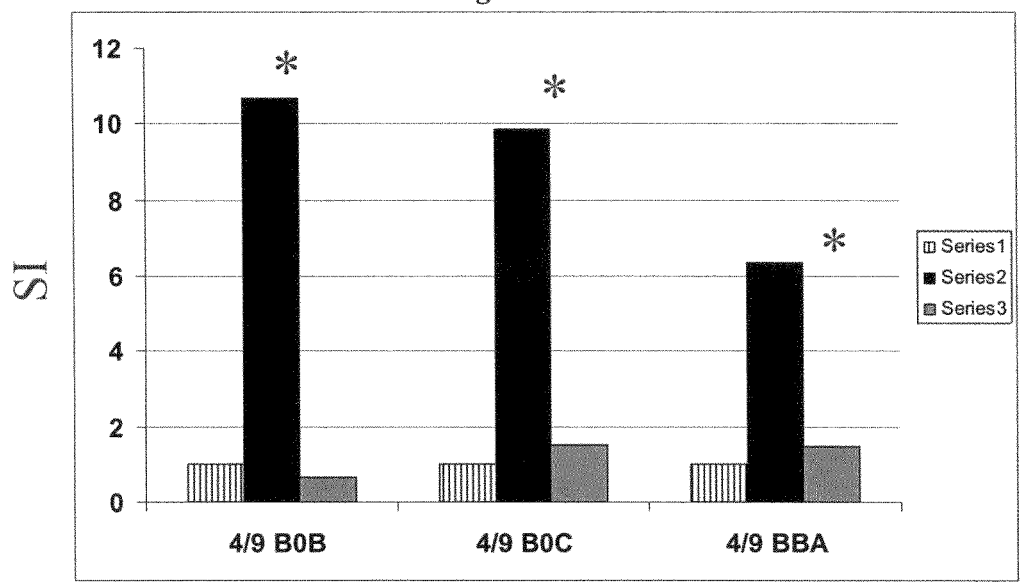

METHODS FOR TREATING AUTOIMMUNE DISEASE BY INDUCING AUTOANTIGEN-SPECIFIC REGULATORY CD4+ T CELLS

CLAIM OF PRIORITY

This application is a continuation-in-part of International Patent Application No. PCT/US2007/067396, filed Apr. 25, 2007, which claims the benefit of U.S. Provisional Patent Application Ser. No. 60/794,802, filed on Apr. 25, 2006. The entire contents of the foregoing are hereby incorporated by reference.

FEDERALLY SPONSORED RESEARCH OR DEVELOPMENT

This invention was made with Government support under Grant No. N01-AI-15416 awarded by the National Institutes of Health. The Government has certain rights in the invention.

TECHNICAL FIELD

This invention relates to methods for the diagnosis and treatment of autoimmune diseases such as diabetes.

BACKGROUND

Autoimmune disease results from an abnormal immune response to self-antigens. At present, treatments which seek to stem the progress of human autoimmune disease are based on the general suppression of all immune responses, which can lead to long-term toxicities and suppression of protective immune responses against pathogens. There is a need for more specific therapeutic strategies to restore immune tolerance to the specific autoantigens implicated in the disease pathology.

Insulin, which is a β-cell specific major protein, is central to the disease process in Type 1 diabetes mellitus (Nakayama et al., Nature 435:220-223 (2005); Kent et al., Nature 435:224-228 (2005)). Insulin is also moderately immunogenic when used alone, and a pilot human trial suggested that it may have the effect of delaying the development of diabetes mellitus (Keller et al., Lancet 341:927-928 (1993)). Intensive insulin therapy may preserve residual beta cell functions (Shah et al., The New England Journal of Medicine 320:550-554 (1999)). However, it must be injected daily over long periods of time to induce the desired effect. Also, the use of insulin raises concerns about hypoglycemia and its sequelae.

Reintroduction of an autoantigen, such as insulin B chain, in incomplete Freund's adjuvant (IFA), has been used in animal models of diabetes, such as NOD mice (Muir et al. (1995) J. Clin. Invest. 95:628-634; Orban et al. (1999) Diabetes 48 (Supp.1):A216-A217; Ramiya et al. (1996) J. Autoimmun. 9:349-356).

SUMMARY

At least in part, the present invention is based on the discovery that immunization with an insulin autoantigen, e.g., the insulin B-chain, leads to the development of insulin autoantigen-specific, e.g., insulin B-chain-specific, regulatory T-cell clones. One aspect of the invention features methods for the prevention or treatment of autoimmune associated diabetes, such as type 1 diabetes (T1DM). The methods include inducing insulin autoantigen-specific, e.g., insulin B-chain-specific, regulatory T cells in a human subject (e.g., a human), by administering to the subject a composition that includes an insulin autoantigen, e.g., insulin B-chain, in a water-in-oil emulsion adjuvant that induces a robust Th-2 biased immune response, and maintaining the regulatory T cell levels in the subject by administering booster doses of the adjuvanted autoantigen. Thus the methods can include obtaining a sample comprising PBMCs from a subject to whom the adjuvanted autoantigen composition has been administered, and quantifying the autoantigen-specific regulatory T cells in the sample (which indicates levels of said cells in the subject), and administering additional doses of the adjuvanted autoantigen composition to maintain a therapeutic level of regulatory T cells. In the alternative or in addition, the methods can simply include administering the adjuvanted autoantigen composition on a regular schedule, e.g., every 12 weeks, or every 24 weeks, to maintain a therapeutic level of Tregs. (As used herein, a "therapeutic level of Tregs" can be a level sufficient to suppress the cytotoxic autoantigen-specific immune response; in the case of autoimmune diabetes, a therapeutic amount would be sufficient to slow or stop the autoimmune destruction of pancreatic islet beta cells.)

In some embodiments, the induced regulatory T cells are CD4+. In some embodiments, the regulatory T cells are also CD25+ and/or FoxP3+. The regulatory T cells may secrete either or both of IL-10 or TGF-beta1 in response to stimulation with the insulin autoantigen. In the methods described herein, "administration" refers to parenteral administration, i.e., not through the alimentary canal but rather by injection through some other route, e.g., subcutaneous, intramuscular, intraorbital, intracapsular, intraspinal, intrasternal, or intravenous.

In some embodiments, the subject has, or is at risk for, autoimmune diabetes, e.g., T1DM. The subject may exhibit autoimmunity against a human insulin autoantigen or fragment thereof, e.g., the insulin B-chain (amino acids 25-54 of SEQ ID NO: 1). Some of the subjects may retain a population of functional, insulin-producing beta cells (functional cells are those that retain the ability to secrete insulin in a glucose-sensitive manner). In some instances, the subject may have no or very few functional beta cells.

In a further aspect, the methods described herein include detecting the presence of autoantigen-specific, e.g., insulin-specific, e.g., insulin B-chain specific, regulatory CD4+ T cells in the subject, e.g., in the blood of a subject, e.g., a vaccinated subject or a subject at risk of developing T1DM, and optionally quantifying the number of such cells present. The presence and/or quantity of the regulatory T cells is an indication that that subject is less likely to develop (advanced) autoimmune disease, e.g., T1DM, despite evidence of ongoing autoimmunity. In addition, the presence and/or quantity of the cells can be used to identify those who have responded or are likely respond to treatment methods (e.g., methods described herein), as the presence and/or quantity and/or function of these cells provides a direct readout of the effect of the treatment and thus can be used instead of, or alternatively in addition to, a marker of residual beta cell function, such as C-peptide.

In some embodiments, the methods described herein include detecting the presence of insulin autoantigen-specific cytotoxic CD8+ T cells in the subject, e.g., in the blood of a subject, e.g., a subject at risk of developing T1DM, and optionally quantifying the number of such cells present. The presence and/or quantity of the CD8+ T cells is an indication that that subject is likely to develop (advanced) autoimmune diabetes, e.g., T1DM, and provides evidence of ongoing autoimmunity. In some embodiments, the methods include selecting a subject who exhibits a detectable population of insulin autoantigen-specific cytotoxic CD8+ T cells, and administering to the subject an adjuvanted autoantigen composition as described herein.

In some embodiments, levels of insulin autoantigen-specific cytotoxic CD8+ T cells and insulin autoantigen-specific regulatory CD4+ T cells can be monitored over time, e.g., before and after administration of a treatment such as the methods described herein, e.g., the administration of an adjuvanted autoantigen composition as described herein. A drop in CD8+ cells with a comcomitant increase in CD4+ cells is indicative of an effective treatment.

As described herein, insulin autoantigen-specific, e.g., B-chain-specific, regulatory CD4+ T cells, either naturally occurring (e.g., generated de novo or expanded from an existing population) or stimulated by administration of a composition including an insulin autoantigen, e.g., B-chain, and a water-in-oil emulsion-based adjuvant, as described herein, can be isolated from a mixed population of peripheral blood mononuclear cells (PBMCs), e.g., cells taken from a subject administered an adjuvanted autoantigen as described herein, using methods known in the art. These methods include affinity purification and cell sorting methods, e.g., tetramer sorting or fluorescence activated cell sorting methods. Once isolated, the cells can optionally be expanded in vitro and administered to the same subject they were isolated from, or a different, e.g., type-matched, subject, as needed, thereby providing a T1DM-specific cell therapy; the cells can also be administered to more than one person. The cells can be administered to a subject who still retains a population of functional beta cells, or to a subject who does not, e.g., as part of an islet transplantation protocol (e.g., as part of a modified Edmonton protocol) or islet regenerative treatment (e.g., with exanetide). In addition, in the case of autologous cells, there will generally be no need for immunosuppression of the subject.

In another aspect, the invention includes a substantially purified population of isolated insulin autoantigen-specific, e.g., B-chain-specific regulatory CD4+ T cells, e.g., human cells, and methods for isolating them. In another aspect, the invention features a composition including the cells described herein in a suitable carrier, e.g., culture media or phosphate buffered saline (PBS). A "substantially pure" population is at least 60% pure, e.g., at least 65%, 70%, 75%, 80%, 85%, 90%, 95%, or more pure. In some embodiments, the cells are also CD25+ and/or FoxP3+. In some embodiments, the cells secrete IL-10 or TGFBeta-1, or both IL10 and TGFBeta in response to stimulation with the appropriate insulin autoantigen.

In some embodiments, the number or presence of insulin autoantigen-specific, e.g., B-chain-specific regulatory CD4+ T cells in a subject is increased by administering to the subject a composition, e.g., a vaccine, comprising a diabetes type 1 autoantigen, e.g., insulin B chain, and an oil-based carrier, e.g., an oil-based adjuvant, e.g., IFA or other oil-based adjuvant emulsion, e.g., Montanide ISA 51, Montanide 801, MAS-1, or an equivalent composition. In preferred embodiments, the oil-based carrier or adjuvant, and preferably the composition, does not include a bacterial component, such as a mycobacterial component.

In general, the subjects in the methods described herein are mammals, e.g., humans, and the autoantigen-specific regulatory cells are mammalian in origin.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 is a line graph illustrating the T cell stimulation index (SI) in T cells from subjects immunized with Insulin B-chain. The cells were stimulated with the whole insulin B-chain. Data shown is Mean+SE; p=0.004 at 24 weeks.

FIG. 2 is a line graph illustrating the T cell stimulation index (SI) in T cells from subjects immunized with Insulin B-chain. The cells were stimulated with insulin B-chain peptide 5-20. Data shown is Mean+SE; p=0.034 at 52 weeks.

FIG. 3 is a line graph illustrating the T cell stimulation index (SI) in T cells from subjects immunized with Insulin B-chain. The cells were stimulated with insulin B-chain peptide 9-23. Data shown is Mean+SE; p=0.032 at 52 weeks.

FIGS. 7A-D are dot plots showing the results of cell sorting experiments. 7A and 7B, sorting by forward scatter (FSC) and side scatter (SSC). 7C, sorting by 0401/B chain-PE and CD4-FITC; 7D, sorting by 0401/B5-20-PE and CD4-FITC.

FIGS. 8A-B are dot plots showing the result of 4/9 Peripheral Blood Mononuclear Cells (PBMC) and 4/9 B chain stimulated cultured cells sorted using tetramer staining. Two clones are shown, sorted by 0401/B5-20-PE and CD4-FITC.

FIG. 9 is a bar graph showing the results of an antigen stimulation assay for the confirmation of the specificity of the clones. The clones were stimulated without antigen (striped bar), with B chain (black bar) and Tetanus toxoid (gray bar). *p<0.05

DETAILED DESCRIPTION

Figure 4:
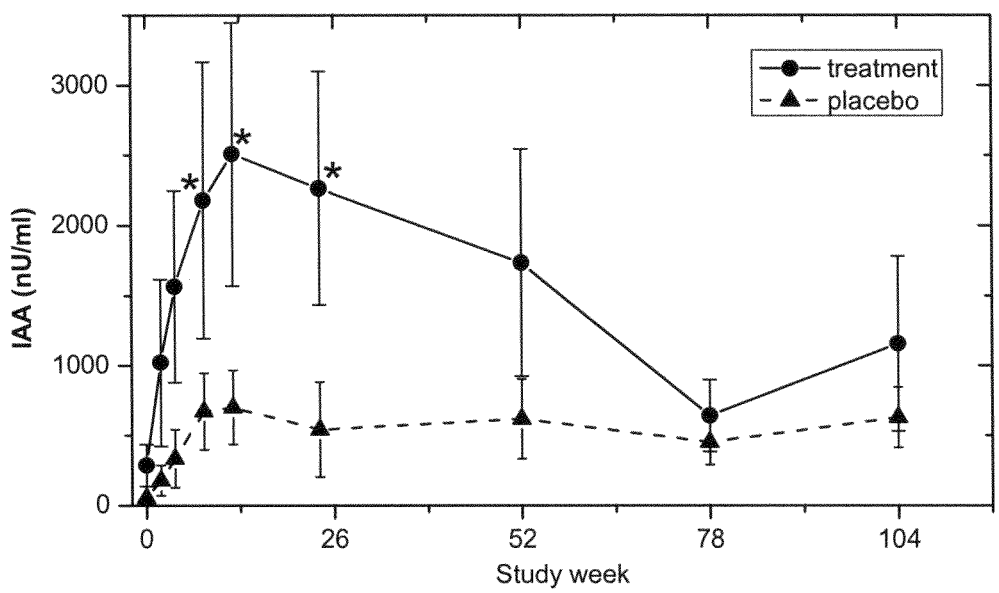
FIG. 4 is a line graph illustrating the humoral immune response in treated human subjects showing insulin autoantibodies (IAA) in: insulin B-chain vaccinated patients, IBC-VS01, and placebo vaccinated patients, VS02. Significant difference of p=0.03 at 12 weeks.

Described herein are methods that include administering, to a subject who exhibits autoantibodies to an autoantigen associated with an autoimmune disease, an autoantigen vaccine comprising an autoantigen associated with the particular autoimmune disease. The autoantigen vaccine includes the autoantigen formulated in a water-in-oil emulsion adjuvant that induces a robust Th2 biased immune response. The administration of the autoantigen vaccine stimulates or induces in the subject the production of regulatory T cells specific to the autoantigen of the vaccine. Without wishing to be bound by theory, it appears that the autoantigen reactive regulatory T cells are involved in a protective process that slows or prevents the autoimmune-mediated destruction of cells containing the autoantigen. The methods further comprise monitoring levels in the subject of the induced autoantigen specific regulatory T cells and re-administering the autoantigen vaccine as a booster at a suitable time and in an amount sufficient to induce autoantigen specific regulatory T cells and to maintain the level and function of such induced T cells so as to effect the progression of the autoimmune disease.

Subjects having autoimmune diseases in general will benefit from the methods described herein and the immunotherapeutic treatment involving the antigen-specific induction of regulatory T cells as a means to treat autoimmune disease. There are autoantigens specifically implicated for each specific autoimmune disease which may be useful in the antigen specific immunotherapy methods described herein. For example:

Multiple Sclerosis

Most autoantigens implicated in MS are expressed not only in the central nervous system but also in the thymus and the periphery. MS-associated antigens include MBP (myelin basic protein, Steinman et al., Mol. Med. Today, 1:79 (1995); Warren et al., 1995, Proc. Natl. Acad. Sci. USA, 92:11061); PLP, transaldolase, 2',3' cyclic nucleotide 3' phosphodiesterases (CNP); MOG and MAG (Steinman, 1995, Nature, 375:739);

Rheumatoid Arthritis

Collagen Type II (Anthony, D. D., Heeger, P. S., Haggi, T. M. (2001) Clin. Exp. Rheumatol. 4: 385-394; Strid, J., Tan, L. A. Strobel, S., Londei, M., Callard, R. (200p7) PLoSS ONE 347) and hsp 60 have both been implicated in the development of RA (Trentham et al., Science 261:1727-1730 (1993); MacHt et al., Immunology 99:208-214 (2000)). Heat shock proteins (hsp) are highly conserved, immune-dominant microbial proteins, whose expression is increased at sites of inflammation. In the experimental model of adjuvant arthritis (AA) immune responses to hsp determine the outcome of disease. AA can be transferred with a single T cell clone specific for a sequence of mycobacterial hsp65 (Mhsp65). Immunization with whole Mhsp65 on the other hand, protects in virtually all forms of experimental arthritis, including AA. This protective effect seems the consequence of the induction of a T cell response directed against self-hsp60. A DNA vaccine encoding human hsp 60 as well as peptide vaccination inhibited AA (Quintana et al., (2002). J. Immunol. 169:3422). A similar protective effect of self-hsp60-specific T cells seems present in patients with a spontaneous remitting form of juvenile idiopathic arthritis. Nasal administration of hsp60 peptides induces IL-10-driven regulatory T cells that are highly effective in suppressing arthritis. Thus hsp60, or peptides derived from hsp60, are suitable candidates for immune therapy in chronic arthritis (Prakken et al. (2003) 25(1):47-63). This may be relevant for human rheumatoid arthritis (RA), where T cell responses to hsp60 and hsp65 have been described (van Roon et al. (1997) J. Clin. Invest. 100:459-163). In both collagen-induced arthritis (CIA) and rheumatoid arthritis, T cells recognize a galactosylated peptide from type II collagen (CII). Soluble MHC II ($A^q$) molecules, complexed with the immunodominant CII259-273 galactosylated peptide, have both preventive and therapeutic effects on arthritis (Dzhambazov et al. (2006) J. Immunol. 176: 1525-1533).

Myasthenia Gravis

Myasthenia gravis (MG) and experimental autoimmune MG (EAMG) are T cell-dependent, antibody-mediated autoimmune diseases. A dual altered peptide ligand (APL) that is composed of the tandemly arranged two single amino acid analogues of two myasthenogenic nicotinic ACh receptor peptides, p195-212 and p259-271, was shown to down-regulate T cell responses to AChR in vitro and in vivo. The dual APL acts by up-regulating CD4+ CD25+ cells expressing characteristic regulatory markers along with an associated increase in levels of IL-10 and TGF-beta. (Aruna et al. (2006) J. Neuroimmunol. 177:63-75.

Systemic Lupus Erythematosus (SLE)

SLE is an autoimmune disease characterized by autoantibodies and systemic clinical manifestations. The autoantigenic epitopes appear to be derived from diverse sources such as nucleosome core histones, ribonucleoproteins, and immunoglobulin variable regions. A peptide, designated hCDR1, based on the complementarity-determining region (CDR) 1 of an autoantibody, ameliorated the serological and clinical manifestations of lupus in both spontaneous and induced murine models of lupus. Thus, hCDR1 ameliorates lupus through the induction of CD4+ CD25+ cells that suppress activation of the autoreactive cells and trigger the up-regulation of TGF-beta. Inflammation in organ-specific autoimmune diseases like T1DM and RA is mostly mediated by Th-1 cytokines, whereas both type 1 and type 2 cytokines appear to be important for tissue damage in SLE. Other autoantigens include calreticulin/Ro/SS-A (Lux et al., J Clin Invest. 89(6): 1945-1951 (1992); Kishore et al, Clin. Exp. Immunol. 108(2):181-190 (2003); nucleosomes (e.g., GenBank Accession No. D28394; Bruggen et al., Ann. Med. Interne (Paris), 147:485-489 (1996)) and the 44,000 Da peptide component of ocular tissue cross-reactive with *O. volvulus* antigen (McKeclmie et al., Ann Trop. Med. Parasitol. 87:649-652 (1993)).

Other autoimmune disease and polypeptides that have been implicated as autoantigens involved in their genesis include: Autoimmune ovarian failure: 3-beta-hydroxysteroid dehydrogenase; Graves' thyroiditis: thyroglobulin, thyroid peroxidase, and thyroid stimulating hormone receptor; Hashimoto's thyroiditis: thyroglobulin and thyroid peroxidase; Primary hypothyroidism: thyroglobulin and thyroid peroxidase; Coeliac disease: transglutaminase; Primary biliary cirrhosis: pyruvate dehydrogenase; Autoimmune hepatitis: cytochrome P4502D6; Addison's disease: 21-alphahydroxylase; Vitiligo: tyrosinase; Anti-glomerular basement membrane disease (Goodpasture's syndrome): type IV collagen; and Systemic sclerosis: Scl-70.

The autoantigens described herein for the specific autoimmune diseases and other autoantigens, known or to be discovered, may be used in the present methods in a way similar to that demonstrated herein, e.g., exemplified by administration of an autoantigen vaccine comprising human insulin B chain formulated in a suitable water-in-oil emulsion to treat human subjects with T1DM.

Methods of Treating Type 1 Diabetes Mellitus

Despite the significant progress that has been made in its treatment, autoimmune associated diabetes places a severe burden on affected individuals as well as on society. Insulin dependent diabetes mellitus (Type 1 diabetes) is an autoimmune disease, in which insulitis leads to the destruction of pancreatic β-cells. At the time of clinical onset of type 1 diabetes, significant numbers of insulin producing β cells are destroyed, leaving only about 15% to 40% still capable of insulin production (McCulloch et al. (1991) Diabetes, 40:673-679). This β-cell failure results in a life long dependence on daily insulin injections and development of the acute and late complications of the disease. During the natural history of the disease, the remaining functional population of β-cells inevitably dies, rendering the patients dependent on exogenous insulin for life. The arrest or even the slowing of further destruction of β-cells would lead to prolonged remission period and delay diabetes-related complications.

Although the Examples described herein focus on autoimmune diabetes and the insulin B chain autoantigen, other diabetes autoantigens can also be used, and other autoimmune diseases can be treated as described herein. Thus the scope of the invention comprises methods and compositions that use or generate or expand regulatory T-cells that are reactive to one or more autoantigens. For diabetes autoantigens, see, e.g., U.S. Patent App. Pub. No. 2003-0045467, and WO2004110373, incorporated herein by reference in their entirety. In a preferred embodiment, the diabetes autoantigen is the insulin B chain (amino acids 25-54 of SEQ ID NO:1).

Vaccination and Monitoring Methods

As demonstrated herein, human insulin B-chain vaccination in subjects with T1DM generates or expands autoantigen (insulin B-chain) specific regulatory CD4+ T cells. These cells have the capacity to "home" to the islet (recognizing the insulin B-chain), where they release regulatory cytokines and perform other cell to cell regulatory functions, thus, the methods and compositions described herein can be used to prevent the development or progression of diabetes mellitus, or prevent or delay loss of residual β-cell mass, providing a longer remission period and delaying or preventing the onset of diabetes-related, usually progressive, complications at a later stage of the life. In addition, the methods described herein can be used to predict whether and/or when a subject, e.g., a subject with ongoing anti-insulin autoimmunity, will progress to T1DM, to evaluate a subject's response to a therapeutic intervention or to determine whether a subject should receive a booster administration of the autoantigen formulation.

Therefore the methods described herein include the administration of an autoantigen in an appropriate adjuvant, e.g., insulin B chain in an oil-in-water emulsion adjuvant as described herein, in an amount sufficient to generate a response that includes the activation, generation or expansion of regulatory T cells specific for that autoantigen, e.g., insulin B-chain specific Tregs. Once Tregs have been stimulated, the methods further include monitoring the levels of Tregs over time, and administering one or, more additional doses of the adjuvanted autoantigen ("boosters") to maintain autoantigen-specific Treg levels. In some embodiments the methods further include determining a level of autoantigen-specific Tregs after administration of the adjuvanted autoantigen, and monitoring the levels over time to determine when to administer booster doses of the vaccine at such time that the Treg levels begin to fall. In some embodiments booster doses can be administered at predetermined times in order to continue to stimulate T regs.

In some embodiments a desirable level of antigen-specific Tregs is an amount sufficient to suppress cytotoxic T cell function.

Cell Therapy Methods

The methods described herein can also be used to treat, delay or prevent the development or progression of T1DM. The methods of the invention can be used to generate, expand, or stimulate diabetes autoantigen reactive regulatory T-cells in a subject and in certain embodiments the stimulated regulatory T cells can be isolated from a subject, expanded in vitro, and re-introduced into either the same or a different subject. These T cells may be naturally occurring in the subject (e.g., expanded from an existing population), but they can also be stimulated or generated by administration of a diabetes autoantigen, e.g., insulin B chain, e.g., by administering to the subject a composition comprising the diabetes autoantigen, e.g., insulin B chain, in an water-in-oil-based adjuvant, e.g., as described in U.S. Patent App. Pub. No. 2003-0045467 and WO2004110373, incorporated herein by reference in their entirety. The methods further comprise monitoring the levels (and, optionally, function) in the subject of the induced autoantigen specific regulatory T cells and re-administering the autoantigen vaccine as a booster at a suitable time to induce autoantigen specific regulatory T cells and to maintain the level and function of such induced T cells so as to effect the progression of the autoimmune disease.

If the regulatory T cells are isolated from and are to be re-introduced into the same subject (i.e., an autologous transplant), no immune suppression is necessary. If the cells are to be introduced into a different subject (i.e., a heterologous transplant), immune suppression may be necessary, and a good HLA match between the donor and recipient is preferred. If the HLA are substantially matched, the immune system is much less likely to respond adversely. The more HLA proteins that match, the less likely a grafted organ will be rejected by the recipient.

An individual has two of each A, B, Cw, DQ, and DR alleles, where one set of A, B, Cw, DQ, and DR (a "haplotype") is inherited from each parent. Individuals can be homozygous or heterozygous for the A, B, Cw, DQ, and DR haplotypes. A donor cell is considered to be HLA "matched" or "histocompatible" to an intended recipient, provided the donor cells do not express HLA products that are foreign to the recipient. For example, a donor cell that is homozygous for a haplotype such as HLA-A1, -Cw7, -B8 or HLA-A29, -Cw7, -B8, will match a recipient having a heterozygous HLA profile with both HLA-A1, -Cw7, -B8, and HLA-A29, -Cw8, -B65 haplotypes. See, e.g., Hui et al; *Handbook of HLA Typing Techniques*, p. 194 (CRC Press, 1993).

The transplantation methods described herein can include the steps of isolating insulin autoantigen-specific, e.g., insulin B chain-specific, regulatory T cells as described herein, and transferring the cells into a mammal or a patient. Transplantation can involve, for example, transferring the cells into a mammal or a patient by injection of a cell suspension into the mammal or patient, surgical implantation of a cell mass into a tissue or organ of the mammal or patient, or perfusion of a tissue or organ (e.g., the pancreas) with a cell suspension. The route of transferring the cells or transplantation will be determined by the need for the cell to reside in a particular tissue or organ and by the ability of the cell to find and be retained by the desired target tissue or organ. In the case where a transplanted cell is to reside in a particular location, it can be surgically placed into a tissue or organ or simply injected into the bloodstream if the cell has the capability to migrate to the desired target organ.

In some embodiments, the regulatory T cells described herein are transplanted into a subject who still retains some functional beta cells. For example, the cells can be isolated from a newly-diagnosed patient.

In some embodiments, the regulatory T cells described herein are transplanted as part of an islet transplantation procedure, to prevent or delay occurrence or reoccurrence of autoimmune destruction of the transplanted cells. Methods for performing such procedures are known in the art, e.g., the Edmonton Protocol. See, e.g., Ryan et al., Diabetes 50:710-719 (2001); Shapiro et al., N. Eng. J. Med. 355: 1318-1330 (2006).

Determination of the appropriate dose of regulatory T cells is generally made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. For example, populations of cells comprising at least about $10^4$, $10^5$, $10^6$, $10^8$, $10^9$, $10^{10}$, or more purified and expanded regulatory T cells as described herein can be administered, e.g., in one or more doses.

Thus the methods described herein can include the steps of isolating one or more insulin autoantigen-specific, e.g., insulin B chain-specific, T cells as described herein, optionally culturing the cell to expand them as needed obtain a population of cells, and transferring the expanded cells into a mammal or a patient.

Subject Selection

Human patients who may be selected for treatment with the methods of the invention can be categorized into the following groups:

Patients with Newly Diagnosed T1DM.

Patients in this group generally have approximately 20% residual β cell function at the time of diagnosis (Staeva-Vieira et al., Clin. and Exp. Immunol., 148:17-31 (2007)) and comprise the group most likely to show a rapid benefit to vaccination. In the U.S., the incidence is 30,000 to 35,000 new T1DM patients annually. As treatment with the vaccine is expected to be life-long, this pool of patients will thus expand annually by at least 30,000 in the U.S. alone, not including the projected 3% annual increase in the incidence of T1DM.

The incidence/100,000 of T1DM in adults is similar to that for children and young adults (age 1-14=10.3; age 15-29 years=6.8; age 30-49=7.3), and many adults are misdiagnosed with type 2 disease due to the misconception of T1DM as a disease only of children (Mobak et al., Diabet. Med. 11: 650-655 (1994); Bruno et al., Diabetes Care 28 (11):2613-2619 (2005)). Using predictive autoantibody markers, a prospective UK study showed that 30% of younger patients diagnosed with type 2 diabetes in fact may have an underlying autoimmune component and usually progress to insulin dependence within 3 years (Turner et al., Lancet 350:1288-1293 (1997); Devendra et al. BMJ 328: 750-754 (2004)). This is consistent with the estimate that 10% of persons over age 35 diagnosed with phenotypic type 2 diabetes actually have underlying autoimmune diabetes; all of who are candidates for the T1DM vaccine (Stenstrom et al., Diabetes 54:S68-S72 (2005); Leslie et al., Clinical Rev. 91:1654-1659 (2006)), distinct from those with latent autoimmune diabetes in adults (LADA)). This group of misclassified patients and LADA patients can also be expected to greatly benefit from treatment with the methods described herein especially since their disease progression takes a little longer to develop. (The insulin B-chain specific T regs induced or activated by the methods described herein, like other antigen specific T regs, can influence effector-autoagressive T cells of other antigen specificity by so called "infectious tolerance" and or "bystander" effects, which in the case of LADA patients may be particularly beneficial.) Correct diagnosis/identification of these patients can be accomplished by methods known in the art, e.g., serum autoantibody assays performed according to AMA Guidelines (available from Quest Diagnostics and ARUP Labs).

Patients with Established T1DM.

There were an estimated 1.8 million (all age groups) T1DM patients (excluding 10% of patients diagnosed with type 2 diabetes but having underlying LADA) in the U.S in 2003. Although such patients have insufficient insulin production and must be maintained on insulin therapy in the face of an ongoing anti-β islet cell autoimmune response, some possess measurable levels of β cells even many years after diagnosis. Importantly, these patients retain the capacity for regenerating functional β cell activity, and it has been suggested that intervention could enable repletion of β cells, possibly to physiologically meaningful levels (Staeva-Vieira et al., (2007) supra). In the active disease state, this potential is insufficient to overcome the ongoing loss of β cells due to the autoimmune response; however, control of the autoimmune attack on β cells would permit P cell regeneration and concomitant restoration of clinically significant insulin production. As the underlying mechanism of autoimmune destruction of β cells is the same at all stages of the disease, patients with established T1DM have the potential of benefiting from vaccine-induced down-regulation of their autoimmune response.

In addition, the methods described herein can be used in patients who receive a transplant of islet β cells; such transplants, without immunosuppression, are unlikely to be successful in the presence of an ongoing autoimmune response against β cells. In addition, for similar reasons the methods described herein will be beneficial when used with islet cell regeneration therapies, e.g., administration of exanetide.

Individuals with a High Risk of Developing T1DM.

The average risk of a child developing T1DM is 6% if either of the child's parents or siblings have the disease compared with 0.4% risk in the general population (Tillil and Kobberling, Diabetes, 36:93-99 (1987)). This represents an estimated 360,000 at risk individuals under the age of 15, and 1.3 million at risk individuals for all age groups in the US in 2007. Early intervention has been suggested as a strategy to enhance the probability of successful therapy (Staeva-Vieira et al., (2007), supra). Screening high risk individuals for antibodies to insulin (IAA), glutamic acid decarboxylase (GAD), and insulinoma associated antigen (IA-2A) provides a reliable method of predicting the development of T1DM (Leslie et al., Diabetologia 42:3-14 (1999); Bingley, Diabetes Care 24:398 (2001); Achenbach, Curr. Diabetes Rep. 5:98-103 (2005)), which can be used to identify candidates for immunization to prevent, or potentially reverse, autoimmune pathology prior to significant β cell destruction. Identification of these individuals can be accomplished using methods known in the art, e.g., by serum autoantibody assays performed according to AMA Guidelines (e.g., assays available from Quest Diagnostics and ARUP Labs).

As used herein, "T1DM" also includes LADA (latent autoimmune diabetes in adults), and subjects who can be treated using the methods described herein include those with LADA.

Diabetes Autoantigens

Exemplary antigens associated with diabetes include GAD65 (glutamic acid decarboxylase 65-Baekkeskov et al., Nature 1990, 347:151), insulin (Palmer et al., Science 1983, 222:1337), and ICA512/IA-2 (islet cell antigen 512; Rabin et al., J. Immunol. 1994, 152:3183).

Autoantibodies against insulin, glutamic acid decarboxylase (GAD), and other islet cell autoantigens, e.g., ICA 512/IA-2 protein tyrosine phosphatase, ICA12, and ICA69, are frequently found in newly diagnosed diabetic patients. Thus, type 1 diabetes autoantigens useful in the methods described herein include, e.g., preproinsulin or an immunologically active fragment thereof (e.g., insulin B-chain, A chain, C peptide or an immunologically active fragment thereof), and other islet cell autoantigens (ICA), e.g., GAD65, islet tyrosine phosphatase ICA512/IA-2, ICA12, ICA69 or immunologically active fragments thereof. Other type 1 diabetes autoantigens include HSP60, carboxypeptidase H, peripherin, gangliosides (e.g., GM1-2, GM3), or immunologically active fragments thereof. Any of the type 1 diabetes autoantigens known in the art or described herein, or immunologically active fragments, analogs or derivatives thereof, are useful in the methods and compositions described herein.

Insulin, Preproinsulin, Proinsulin, and Fragments Thereof

Autoantibodies against insulin are frequently found in newly diagnosed diabetic patients. The insulin mRNA is translated as a 110 amino acid single chain precursor called preproinsulin, and removal of its signal peptide during insertion into the endoplasmic reticulum generates proinsulin. Proinsulin consists of three domains: an amino-terminal B chain, a carboxy-terminal A chain and a connecting peptide in the middle known as the C peptide. Within the endoplasmic reticulum, proinsulin is exposed to several specific endopeptidases which excise the C peptide, thereby generating the mature form of insulin which consists of the A and B chain. Insulin and free C peptide are packaged in the Golgi into secretory granules which accumulate in the cytoplasm. The preproinsulin peptide sequence is as follows, with the B chain underlined:

```
                                              (SEQ ID NO:1)
MALWMRLLPL LALLALWGPD PAAAFVNQHL CGSHLVEALY

LVCGERGFFY TPKTRREAED LQVGQVELGG GPGAGSLQPL

ALEGSLQKRG IVEQCCTSIC SLYQLENYCN
```

Insulin A chain includes amino acids 90-110 of SEQ ID NO:1. B chain includes amino acids 25-54 of SEQ ID NO: 1. The connecting sequence (amino acids 55-89 of SEQ ID NO:1) includes a pair of basic amino acids at either end. Proteolytic cleavage of proinsulin at these dibasic sequences liberates the insulin molecule and free C peptide, which includes amino acids 57-87 of SEQ ID NO:1. The human preproinsulin or an immunologically active fragment thereof, e.g., B chain or an immunogenic fragment thereof, e.g., amino acids 33-47 of SEQ ID NO: 1 (corresponding to residues 9-23 of the B-chain), are useful as autoantigens in the methods and compositions described herein.

Engineered fragments of insulin can also be used, e.g., engineered insulin dimers as described in WO2004110373, or U.S. Patent Application Publication No. 20070225210, each incorporated herein by reference in its entirety.

GAD65

GAD65 is a primary β-cell antigen involved in the autoimmune response leading to insulin dependent diabetes mellitus (Christgau et al. (1991) J Biol. Chem. 266(31): 21257-64). The presence of autoantibodies to GAD65 is used as a method of diagnosis of type 1 diabetes. GAD65 is a 585 amino acid protein as follows (SEQ ID NO:2).

```
                                              (SEQ ID NO:2)
MASPGSGFWS FGSEDGSGDS ENPGTARAWC QVAQKFTGGI

GNKLCALLYG DAEKPAESGG SQPPPAAARK AACACDQKPC

SCSKVDVNYA FLHATDLLPA CDGERPTLAF LQDVMNILLQ

YVVKSFDRST KVIDFHYPNE LLQEYNWELA DQPQNLEEIL

MHCQTTLKYA IKTGHPRYFN QLSTGLDMVG LAADWLTSTA

NTNMFTYEIA PVFVLLEYVT LKKMREIIGW PGGSGDGIFS

PGGAISNMYA MMIARFKMFP EVKEKGMAAL PRLIAFTSEH

SHFSLKKGAA ALGIGTDSVI LIKCDERGKM IPSDLERRIL

EAKQKGFVPF LVSATAGTTV YGAFDPLLAV ADICKKYKIW

MHVDAAWGGG LLMSRKHKWK LSGVERANSV TWNPHKMMGV

PLQCSALLVR EEGLMQNCNQ MHASYLFQQD KHYDLSYDTG

DKALQCGRHV DVFKLWLMWR AKGTTGFEAH VDKCLELAEY

LYNIIKNREG YEMVFDGKPQ HTNVCFWYIP PSLRTLEDNE

ERMSRLSKVA PVIKARMMEY GTTMVSYQPL GDKVNFFRMV

ISNPAATHQD IDFLIEEIER LGQDL
```

Islet Tyrosine Phosphatase IA-2

IA-2/ICA512, a member of the protein tyrosine phosphatase family, is another major autoantigen in type 1 diabetes (Lan et al. DNA Cell. Biol. 13:505-514, 1994). 70% of diabetic patients have autoantibodies to IA-2, which appear years before the development of clinical disease. The IA-2 molecule (SEQ ID NO:3, below) is 979 amino acids in length and consists of an intracellular, transmembrane, and extracellular domain (Rabin et al. (1994) J. Immunol. 152 (6), 3183-3188). Autoantibodies are typically directed to the intracellular domain, e.g., amino acids 600-979 of SEQ ID NO:3 and fragments thereof (Zhang et al. (1997) Diabetes 46:40-43; Xie et al. (1997) J. Immunol. 159:3662-3667). The amino acid sequence of IA-2 is as follows.

```
                                              (SEQ ID NO:3)
MRRPRRPGGLGGSGGLRLLLCLLLLSSRPGGCSAVSAHGCLFDRRLCSHL

EVCIQDGLFGQCQVGVGQARPLLQVTSPVLQRLQGVLRQLMSQGLSWHDD

LTQYVISQEMERIPRLRPPEPRPRDRSGLAPKRPGPAGELLLQDIPTGSA

PAAQHRLPQPPVGKGGAGASSSLSPLQAELLPPLLEHLLLPPQPPHPSLS

YEPALLQPYLFHQFGSRDGSRVSEGSPGMVSVGPLPKAEAPALFSRTASK
```

-continued

```
GIFGDHPGHSYGDLPGPSPAQLFQDSGLLYLAQELPAPSRARVPRLPEQG

SSSRAEDSPEGYEKEGLGDRGEKPASPAVQPDAALQRLAAVLAGYGVELR

QLTPEQLSTLLTLLQLLPKGAGRNPGGVVNVGADIKKTMEGPVEGRDTAE

LPARTSPMPGHPTASPTSSEVQQVPSPVSSEPPKAARPPVTPVLLEKKSP

LGQSQPTVAGQPSARPAAEEYGYIVTDQKPLSLAAGVKLLEILAEHVHMS

SGSFINISVVGPALTFRIRHNEQNLSLADVTQQAGLVKSELEAQTGLQIL

QTGVGQREEAAAVLPQTAHSTSPMRSVLLTLVALAGVAGLLVALAVALCV

RQHARQQDKERLAALGPEGAHGDTTFEYQDLCRQHMATKSLFNRAEGPPE

PSRVSSVSSQFSDAAQASPSSHSSTPSWCEEPAQANMDISTGHMILAYME

DHLRNRDRLAKEWQALCAYQAEPNTCATAQGEGNIKKNRHPDFLPYDHAR

IKLKVESSPSRSDYINASPIIEHDPRMPAYIATQGPLSHTIADFWQMVWE

SGCTVIVMLTPLVEDGVKQCDRYWPDEGASLYHVYEVNLVSEHIWCEDFL

VRSFYLKNVQTQETRTLTQFHFLSWPAEGTPASTRPLLDFRRKVNKCYRG

RSCPIIVHCSDGAGRTGTYILIDMVLNRMAKGVKEIDIAATLEHVRDQRP

GLVRSKDQFEFALTAVAEEVNAILKALPQ
```

ICA12

ICA 12 (Kasimiotis et al. (2000) Diabetes 49(4):555-61; Gen bank Accession No. AAD16237; SEQ ID NO:4) is one of a number of islet cell autoantigens associated with diabetes. The sequence of ICA12 is as follows.

```
                                           (SEQ ID NO:4)
MSMRSPISAQ LALDGVGTMV NCTIKSEEKK EPCHEAPQGS

ATAAEPQPGD PAPASQDSAD PQAPAQGNFR GSWDCSSPEG

NGSPEPKRPG ASEAASGSQE KLDFNRNLKE VVPAIEKLLS

SDWKERFLGR NSMEAKDVKG TQESLAEKEL QLLVMIHQLS

TLRDQLLTAH SEQKNMAAML FEKQQQQMEL ARQQQEQIAK

QQQQLIQQQH KINLLQQQIQ QVNMPYVMIP AFPPSHQPLP

VTPDSQLALP IQPIPCKPVE YPLQLLHSPP APVVKRPGAM

ATHHPLQEPS QPLNLTAKPK APELPNTSSS PSLKMSSCVP

RPPSHGGPTR DLQSSPPSLP LGFLGEGDAV TKAIQDARQL

LHSHSGALDG SPNTPFRKDL ISLDSSPAKE RLEDGCVHPL

EEAMLSCDMD GSRHFPESRN SSHIKRPMNA FMVWAKDERR

KILQAFPDMH NSSISKILGS RWKSMTNQEK QPYYEEQARL

SRQHLEKYPD YKYKPRPKRT CIVEGKRLRV GEYKALMRTR

RQDARQSYVI PPQAGQVQMS SSDVLYPRAA GMPLAQPLVE

HYVPRSLDPN MPVIVNTCSL REEGEGTDDR HSVADGEMYR

YSEDEDSEGE EKSDGELVVL TD
```

ICA69

ICA69 is another autoantigen associated with type 1 diabetes (Pietropaolo et al. J. Clin. Invest. 1993; 92:359-371). The amino acid sequence of ICA69 is as follows.

```
                                           (SEQ ID NO:5)
MSGHKCSYPW DLQDRYAQDK SVVNKMQQRY WETKQAFIKA

TGKKEDEHVV ASDADLDAKL ELFHSIQRTC LDLSKAIVLY

QKRICFLSQE ENELGKFLRS QGFQDKTRAG KMMQATGKAL

CFSSQQRLAL RNPLCRFHQE VETFRHRAIS DTWLTVNRME

QCRTEYRGAL LWMKDVSQEL DPDLYKQMEK FRKVQTQVRL

AKKNFDKLKM DVCQKVDLLG ASRCNLLSHM LATYQTTLLH

FWEKTSHTMA AIHESFKGYQ PYEFTTLKSL QDPMKKLVEK

EEKKKINQQE STDAAVQEPS QLISLEEENQ RKESSSFKTE

DGKSILSALD KGSTHTACSG PIDELLDMKS EEGACLGPVA

GTPEPEGADK DDLLLLSEIF NASSLEEGEF SKEWAAVFGD

GQVKEPVPTM ALGEPDPKAQ TGSGFLPSQL LDQNMKDLQA

SLQEPAKAAS DLTAWFSLFA DLDPLSNPDA VGKTDKEHEL

LNA
```

Glima38

Glima 38 is a 38 kDa islet cell membrane autoantigen which is specifically immunoprecipitated with sera from a subset of prediabetic individuals and newly diagnosed type 1 diabetic patients. Glima 38 is an amphiphilic membrane glycoprotein, specifically expressed in islet and neuronal cell lines, and thus shares the neuroendocrine expression patterns of GAD65 and IA2 (Aanstoot et al. J. Clin. Invest. 1996 Jun. 15; 97(12):2772-2783).

Heat Shock Protein 60 (HSP60)

HSP60, e.g., an immunologically active fragment of HSP60, e.g., p277 (see Elias et al., Eur. J. Immunol. 1995 25(10):2851-7), can also be used as an autoantigen in the methods and compositions described herein. Other useful epitopes of HSP 60 are described, e.g., in U.S. Pat. No. 6,110,746.

Carboxypeptidase H

Carboxypeptidase H has been identified as an autoantigen, e.g., in pre-type 1 diabetes patients (Castano et al. (1991) J. Clin. Endocrinol. Metab. 73(6):1197-201; Alcalde et al. J. Autoimmun. 1996 August; 9(4):525-8.). Therefore, carboxypeptidase H or immunologically reactive fragments thereof (e.g., the 136-amino acid fragment of carboxypeptidase-H described in Castano, supra) can be used in the methods and compositions described herein.

Peripherin

Peripherin is a 58 KDa diabetes autoantigen identified in NOD mice (Boitard et al. (1992) Proc. Natl. Acad. Sci. U.S.A. 89(1):172-6. The human peripherin sequence is shown as SEQ ID NO:6, below.

```
                                           (SEQ ID NO:6)
MSHHPSGLRA GFSSTSYRRT FGPPPSLSPG AFSYSSSSRF

SSSRLLGSAS PSSSVRLGSF RSPRAGAGAL LRLPSERLDF

SMAEALNQEF LATRSNEKQE LQELNDRFAN FIEKVRFLEQ

QNAALRGELS QARGQEPARA DQLCQQELRE LRRELELLGR

ERDRVQVERD GLAEDLAALK QRLEEETRKR EDAEHNLVLF

RKDVDDATLS RLELERKIES LMDEIEFLKK LHEEELRDLQ

VSVESQQVQQ VEVEATVKPE LTAALRDIRA QYESIAAKNL
```

```
QEAEEWYKSK YADLSDAANR NHEALRQAKQ EMNESRRQIQ

SLTCEVDGLR GTNEALLRQL RELEEQFALE AGGYQAGAAR

LEEELRQLKE EMARHLREYQ ELLNVKMALD IEIATYRKLL

EGEESRISVP VHSFASLNIK TTVPEVEPPQ DSHSRKTVLI

KTIETRNGEQ VVTESQKEQR SELDKSSAHS Y
```

Gangliosides

Gangliosides can also be useful autoantigens in the methods and compositions described herein. Gangliosides are sialic acid-containing glycolipids which are formed by a hydrophobic portion, the ceramide, and a hydrophilic part, i.e. the oligosaccharide chain. Gangliosides are expressed, inter alia, in cytosol membranes of secretory granules of pancreatic islets. Auto-antibodies to gangliosides have been described in type 1 diabetes, e.g., GM1-2 ganglioside is an islet autoantigen in diabetes autoimmunity and is expressed by human native β cells (Dotta et al., Diabetes. 45(9): 1193-6 (1996)). Gangliosides GT3, GD3 and GM-1 are also the target of autoantibodies associated with autoimmune diabetes (reviewed in Dionisi et al., Ann. Ist. Super. Sanita. 33(3):433-5 (1997)). Ganglioside GM3 participates in the pathological conditions of insulin resistance (Tagami et al., J Biol. Chem., J. Biol. Chem. 277 (5): 3085-3092 (2002)).

Adjuvant/Delivery System

The compositions described herein include an autoantigen in a water-in-oil adjuvant with a Th2 bias, wherein the adjuvant is emulsified with the antigen in the water phase.

The selection of an appropriate adjuvant is important in inducing antigen specific regulatory T cells. Freund's adjuvant emulsions, complete Freund's adjuvant (CFA) and incomplete Freund's adjuvant (IFA), have been standards against which other adjuvants have been measured. CFA is not suitable for use in humans, due especially to the intense inflammatory reactions induced by its mycobacterium component; although, IFA has been used in clinical trials, it has not been approved for any human indications. Nevertheless, these water-in oil (W/O) emulsions are generally recognized as potent adjuvants and are used widely in animal studies.

Alum is the only currently U.S.-approved adjuvant with a Th2 bias avoiding cell mediated cytotoxicity, but alum is inadequate as an adjuvant for autoantigen, self-epitope vaccines due to insufficient immunopotency. IFA type adjuvants such as Montanide ISA 51 are mineral oil based. The repeated use of IFAs in treating chronic disease settings with IFAs may result in mineral oil deposits at injection sites and can lead to formation of cysts. IFA emulsions are administered in formulations that have aqueous globules of about 3 to 10, or even 50, microns in diameter.

Mannide monooleate based adjuvants are commercially available, such as Incomplete Freund's Adjuvant (IFA) from a number of sources, and ISA 51 and ISA 720 available from SEPPIC, Paris, France. Water-in-oil type emulsion adjuvants can also be formulated with mannide monooleate which is commercially available from a number of sources (such as Combe, Inc. under the tradename, Arlacel), and squalene and squalane (from several commercial sources). The water-in-oil adjuvants used in the methods and compositions described herein should be formulated so that the aqueous globules in the emulsion carrying the antigen have median diameters less than 1 micron with median diameters in the range from about 100 nanometers to about 1 micron, and typically with an average diameter of about 300 nanometers.

MAS-1 is a mannide monooleate based water-in-oil emulsion adjuvant system comprising naturally occurring and metabolizable biological oils available from Mercia Pharma, Inc. MAS-1 augments immune responses to poorly immunogenic self-antigens in humans without breaking immune self tolerance, thereby avoiding the induction of autoimmunity. MAS-1-based autoantigen vaccines induce robust Th2 biased immune responses, but are much more potent than Alum-based vaccines with self antigens and are comparable to IFA-based vaccines in terms of immunospecificity and immunogenicity. MAS-1 based vaccines well tolerated than after i.m. or s.c. injection. MAS-1 based vaccines have excellent pharmaceutical physico-chemical characteristics. These include homogeneous globule size distribution for efficient antigen presentation, low viscosity to facilitate low volume doses, and extended stability at refrigerated temperatures facilitating distribution through standard cold chain procedures. MAS-1 provides a depot of vaccine to promote efficient immunostimulation, but being metabolizable is cleared from the injection site. MAS-1 emulsions may be produced in formulations with aqueous globules carrying the antigen having median diameters less than 1 micron, and typically about 300 nanometers.

Diagnosis/Prognosis and Evaluation of Therapeutic Interventions

The presence, number, and function of autoantigen-specific Treg cells can be used as an indication of a subject's risk of developing advanced autoimmune disease, or to determine whether a therapeutic intervention is or is likely to be successful. If a subject with an autoimmune disease has a number of Tregs (i.e., Tregs specific for an autoantigen associated with that autoimmune disease) above a threshold, then the subject is less likely to develop advanced disease, whereas a dearth of Tregs may indicate a greater likelihood that the subject's disease will progress. Similarly, a treatment that increases the number of autoantigen-specific Tregs, e.g., above a threshold or above baseline, may be considered effective or likely to be effective in treating or preventing the progression of the disease.

A number of methods known in the art can be used to identify and quantify autoantigen-specific Treg cells. For example, see Bluestone et al., US PG Pub. No. 20050186207; Norment et al., US PG Pub. No. 2006/0063256; Tetramers or CFSE methods can be used, e.g., combined with selection by FACS for T reg markers like CD127 low/negatives or Foxp3; see, e.g., Mallone and Nepom, Clin Immunol 110:232-242 (2004). As one example, a competitive liquid phase radioimmunoassay as described herein can be used (see the Examples, below).

The presence of diabetes autoantigen reactive T-cells in a subject is indicative of a protective process that slows or prevents the autoimmune-mediated destruction of beta cells and islets that is the hallmark of T1DM. Therefore, the presence of these cells indicates a reduced or low risk of developing T1DM. Methods for detecting and quantifying these cells are known in the art and described herein. For example, the cells can be purified using antigen-loaded MHC tetramers as known in the art and described herein, and quantified using known methods, e.g., cell sorting. For example, if the MHC tetramer is fluorescently labeled, FACS can be used.

In addition, the presence and/or number of diabetes autoantigen reactive T-cells can be used to evaluate a therapeutic intervention. For example, the intervention can be a standard or conventional therapy, and, as one example, the methods can be used to determine whether the therapy is effective in a particular subject. Alternatively, the intervention can be an experimental therapy, and the methods can be used to determine whether the therapy is effective in a particular subject and/or in a population of subjects, e.g., in a clinical trial setting. These methods will allow the evaluation of preventive therapies much more quickly than standard methods which rely on the development or non-development in diabetes or significant improvement in C-peptide levels as a statistical end-point and thus require many years of follow-up to determine efficacy. In contrast, the present methods can be used, e.g., after only months, e.g., three, six, nine, or twelve months, thereby considerably shortening the follow-up time.

EXAMPLES

The invention is further described in the following examples, which do not limit the scope of the invention described in the claims.

Example 1: Immunization of Human Subjects with B Chain

Twelve subjects between the ages of 18-35 years who had been newly diagnosed with T1DM (within 3 months of enrollment) and who were determined to be positive for any of the three diabetes autoantibodies (IAA—if tested within 2 weeks of insulin therapy; GAD65Ab, IA2Ab) were enrolled. The inclusion and exclusion criteria were as follows:

Inclusion Criteria:
Age 18-35 years.
Newly diagnosed (<3 months) with type 1 diabetes mellitus which requires treatment with exogenous human insulin.
Positively for any of the three antibodies (IAA, GAD65Ab, or IA2Ab) or if the subject is tested after 2 weeks of starting on insulin treatment then positively of any of the following two antibodies (GAD65Ab and/or IA2Ab).
Signs informed consent.
Exclusion Criteria
Over three months from the time of diagnosis with type 1 diabetes mellitus.
History of treatment with any oral hypoglycemic agent for >3 months duration.
Known severe active disease (e.g., chronic active hepatitis, severe cardiac, renal, hepatic, immunodeficiency) and/or disease, which is likely to limit life expectancy or lead to therapies such as immunosuppression during the time of the study.
A history of or recently positive viral hepatitis test for HBV [with positive HBVsAg, HBVcAg, or HBVeAg], HCV [with a positive Anti-HCV (EIA) and confirmatory HCV RIBA], or a positive HIV-1/2 [(ELISA) with a confirmatory WB] at the screening visit.
A history of or recently positive PPD skin test except for those with a history of BCG immunization.
A significantly abnormal general serum screening lab result defined as a WBC<3.0×103/mL, a Hgb<10.0 g/dL, a platelet count <150×103/mL, a creatinine >1.4× the upper limit of the normal range, an SGOT>2.0× upper limit of the normal range, an SGPT>2.0× upper limit of the normal range, or gross (4+) hematuria present on the screening urinalysis (regardless of menstrual status for female subjects).
Prior participation in trial for prevention of type 1 diabetes mellitus (e.g., nicotinamide, insulin, immunosuppressive drugs). However, individuals known to be in placebo arm of a completed prior prevention trial, if meeting all other criteria, will be eligible.
A history of therapy with immunosuppressive drugs or steroids within past two years for a period of more than 3 months.
Ongoing use of medications known to influence glucose tolerance (i.e., sulfonylureas, metformin, diphenylhydantoin, thiazide or other potassium depleting diuretics, beta-adrenergic blockers, niacin.)
Individuals deemed unable to comply with the protocol.
A history of complications related to routine vaccinations (i.e., DPT, Polio, Td, MMR).
Pregnancy or planned pregnancy within the time frame of the study. Women of childbearing potential are not excluded from participation. Individuals will be advised not to volunteer for the study if they plan to become pregnant during the time of the study. Low dose estrogen oral contraception is permitted. A pregnancy test (serum beta-HCG, ICON II HCG by Hybritech) must be obtained in women of childbearing potential prior to enrollment (at the screening visit and again immediately before administration of the clinical trial material if it has been 2 weeks or longer between the screening visit and the treatment visit).
Individuals with active CMV infection as defined by CMV-specific serology (IgG or IgM) and by positive rapid antigen testing [quantitative PCR], with or without a compatible clinical illness.

All subjects completed all scheduled visits as planned. No significant differences were noted between the two groups in age, BMI, HbA1c, insulin use, autoantibody status and stimulated C-peptide levels. The mean (SEM) ages were 29.0±2.5 years (4 M/2F) and 27.7±2.4 years (5M/1F) in the insulin B-chain vaccinated and placebo groups, respectively; all BMI values were normal. Table A contains a summary of subject demographic data.

TABLE A

Demographic and baseline characteristics at entry

| | Treatment (IBC-VS01) n = 6 | Placebo (VSO2) n = 6 |
| --- | --- | --- |
| Sex | 4M 2F | 5M 1F |
| Age - yr | 29.0 ± 2.5 | 27.7 ± 2.4 |
| BMI - kg/m2 | 21.6 ± 0.5 | 23.5 ± 0.5 |
| DKA - No. present | 2 | 1 |
| Total C-peptide (AUC) (nmol/l) | | |
| Mean | 0.63 ± 0.07 | 0.73 ± 0.07 |
| Median | 0.39 | 0.67 |
| HbA1c - % | 8.4 | 9.1 |
| Daily Insulin Usage - U/kg | 0.32 ± 0.05 | 0.21 ± 0.02 |
| Autoantibodies | | |
| IAA - nU/ml | | |
| mean | 286.6 ± 61.0 | 54.2 ± 5.5 |
| median | 70.1 | 65.9 |
| GAD65 - index | 0.62 ± 0.04 | 0.52 ± 0.06 |
| IA2 - index | 0.69 ± 0.12 | 2.63 ± 0.62 |

Subjects were immunized (1 mL) with a single dose of either insulin B chain (2 mg) formulated in IFA (N=6) or with placebo emulsion (N=6), administered intramuscularly.

Human insulin B-chain was made as a monocomponent, HPLC-purified peptide, synthesized on a Protein Synthesizer model 433A (Applied Biosystems, Foster City, Calif.) using amino acid preparations from Peptide International (Louisville, Ky.). The study drug, IBC-VS01, contained 2 mg insulin B-chain peptide in Montanide ISA51-incomplete Freund's adjuvant (IFA, Seppic Inc., Fairfield, N.J.) in a 50/50 (w/w) emulsion. The placebo was a vehicle control (VS02) consisting of buffer solution (4 M urea in phosphate buffer) in Montanide ISA51-incomplete Freund's adjuvant in a 50/50 (w/w) emulsion. Both study drug and placebo were prepared immediately prior to administration using a point-of-use high-pressure syringe mixing method to a volume of 1 ml.

Subjects were randomly assigned in a 1:1 ratio to receive a single dose of either 2 mg human insulin B-chain in IFA or placebo (IFA) via intramuscular injection. All subjects received the immunization with insulin B chain or placebo and were followed for two years.

Example 2: Antigen Specific T-Cells

To determine the effects of immunization on T cell populations, functional and proliferation assays were performed.

For antigen specific T-cell proliferation assays and cytokine release, peripheral blood mononuclear cells (PBMCs) were isolated from the subjects described in Example 1 and purified as follows. PBMCs were separated from heparinzed blood using Ficoll-Paque Plus (Amersham Biosciences AB, Uppsala, Sweden). Following counting, they were resuspended at a density of $1.32 \times 10^7$ cells/ml in culture medium (RPMI-1640, supplemented with 1% 1M HEPES, 1% Sodium pyruvate, 1% Glutamate, 1% Penicillin/Streptomycin (all from BioWhittaker Cambrex, Walkersville, Md., USA), 1% MEM (non-essential amino acid solution from Gibco, Invitrogen, Grand Island, N.Y.), and 5% heat-inactivated human AB serum (Omega, Tarzana Calif., USA)) for the T cell antigen stimulation assays.

The remaining cells were frozen in heat inactivated human AB serum (Omega) with 10% dimethyl-sulfoxide (DMSO, Sigma-Aldrich, St. Louis, Mo., USA) and stored at −80° C. until assayed.

T cell stimulation assays were performed as follows: Freshly isolated PBMCs were pulsed for 2 hours at 37° C. with the specific antigens (0.01 and 0.1 LfU/ml tetanus toxoid [TT] for positive control, 25 and 50 µg/ml insulin B chain, 10 and 30 µg/ml insulin, 10 and 30 µg/ml proinsulin, 1, 5 and 20 µg/ml GAD65 and overlapping peptides of proinsulin [OP 1-10 (Durinovic-Bello et al., J. Autoimmun. 18:55-66 (2002)), all 40 µg/ml]) and placed into 96-well, round-bottom plates (Corning, USA) at $1.5 \times 10^5$ cells/well. After 4 days incubation at 37° C. and 5% $CO_2$, 100 µl culture medium was changed to 100 µl fresh medium containing 10 U/ml recombinant interleukin-2 (IL-2, Tecin™ Teceleukin—bulk Ro 23-6019, NCI). After 7 days stimulation, the supernatant was collected from each well for use in cytokine assays, while the cells were treated overnight with 1 µci/well $H^3$ thymidine (GE Healthcare). The next day, $H^3$ thymidine incorporation was assessed by a Wallac 1450 MicroBeta TriLux liquid scintillation and luminescence counter (PerkinElmer Inc.). Stimulation index (SI) values were calculated as the ratio of the normalized count per minute (cpm) values of the stimulated and control cells. A SI value of 2 or above is considered positive.

All patients vaccinated with human insulin B-chain developed a robust T cell response to insulin B-chain. This response peaked at 24 weeks, then slowly declined but remained positive for up-to 2 years follow up (FIG. 1). Less prominent responses were detected to proinsulin and some of the insulin B-chain overlapping peptides (B-chain 5-20 and 9-23 peptides, FIGS. 2 and 3). No proinsulin, insulin or insulin peptide-specific T cell responses were detected in the placebo group.

On the other hand, using these assays none of the placebo treated subjects at any time point showed a detectable positive T cell responses to the human insulin B chain (although it is possible that Insulin B-chain specific Tregs were present, but below the level of detection of these assays). The stimulation index for insulin B chain peptide B:5-20 was significantly higher for the treatment group at week 52 (p=0.034); however, the overall difference between groups and between slopes were not statistically significant (p=0.443 and p=0.179, respectively). The stimulation index for insulin B chain peptide B:9-23 did not reach significantly higher values for the treatment group until 52 weeks (p=0.032). Both insulin B chain vaccinated and placebo groups responded similarly to tetanus toxoid antigen used as a positive control for the peripheral blood T cell proliferation assays.

Thus, all six study participants in the insulin B-chain vaccinated group and none in the control group showed a high level of T-cell proliferation in responses to insulin B-chain stimulation. This antigen-specific response reached a zenith at 6 months, then slowly declined, but remained positive for up to 2 years. The stimulation index (SI) at 24 weeks and 52 weeks and the SI ratio for drug product versus placebo for B chain and the related peptides are shown in Table 1.

The T cell proliferative response shows a high degree of specificity for the insulin B chain vaccine, the immunizing antigen. The B:9-23 peptide, reported to be an immunologically dominant region of the insulin B chain, as well as the B:5-20 peptide and proinsulin, exhibited a significantly reduced ability compared to the insulin B chain, to specifically stimulate proliferation of PBMCs from the vaccinated subjects. This suggests that the choice of antigen in the vaccine should as closely as possible match the intact native insulin B chain.

TABLE 1

Specificity of T Cell Stimulation in Immunized Subjects

| | T Cell Stimulation Index (SI) | | | | | | | |
|---|---|---|---|---|---|---|---|---|
| | B chain | | | Proinsulin | | B: 5-20 | | B: 9-23 |
| | Week | | | | | | | |
| | 24 | 52 | 78 | 24 | 52 | 24 | 52 | 24 | 52 |
| Vaccine | 14.0 | 10.2 | 15.5 | 1.9 | 1.7 | 3.3 | 3.3 | 1.6 | 2.1 |
| Placebo | 1.2 | 1.2 | 1.2 | 1.0 | 1.2 | 1.2 | 0.7 | 0.7 | 0.7 |
| Ratio Vaccine/Placebo | 11.7 | 8.5 | 12.9 | 1.9 | 1.4 | 2.7 | 4.7 | 2.3 | 3.0 |

These results indicate that vaccination with human insulin B chain induces a persistent insulin B chain-specific T cell response.

In order to characterize the insulin B-chain-specific T cell response, cytokine (TGF-beta1, IL-10, IL-17, IL-4, IFN-gamma) production was measured in the supernatant of the cell cultures used in the T cell stimulation assay. Briefly, cytokine production from the T cell stimulation assay supernatants was evaluated by a sandwich ELISA using a combination of unlabeled and biotin-labeled monoclonal antibodies to IFN-γ and IL-4 (BD Biosciences PharMingen). Avidin-peroxidase conjugate and TMB substrate (all from BD Biosciences PharMingen) were used to develop the assay. Interleukin-10 (IL-10) was measured with a Human IL-10 ELISA kit (eBioscience, USA), interleukin-17 (IL-17) with a Human IL-17 ELISA Kit (eBioscience, USA), and TGF-beta with the Human TGF-beta1 DuoSet (R&D Systems, USA), all according to the manufacturers' protocols.

Native B-insulin may be formulated as a 30:70 water-in-oil (w/o) emulsion by homogenization of a 30:70 aqueous/oil pre-mix. The continuous oily phase can be prepared from squalene, squalane, or combinations of squalane and squalene suitably formulated with emulsifiers such as Mannide monooleate (MMO), Polyoxyl-40-hydrogenated castor oil (POCO), or similar amphipathic agents and their mixtures. Alternatively, native B-insulin may be formulated as a 50:50 w/o emulsion by homogenization of a 50:50 aqueous/oil pre-mix based on mineral oil formulated with emulsifiers, for example Mannide monooleate, Polyoxyl-40-hydrogenated castor oil, or similar amphipathic agents and their mixtures. Formulations suitable for use as the continuous oily phase in water-in-oil emulsions are available as Montanide formulations from SEPPIC, Paris, France.

In a preferred embodiment, the autoantigen is human insulin B-chain (amino acids 25-54 of SEQ ID NO:1 of US Patent Application No. 2003/0045467) or an immunologically active fragment or variant thereof. In a preferred embodiment, the B-chain or fragment thereof is not recombinant. For example, the B-chain or immunogenic fragment or variant thereof is a synthetic peptide, e.g., made by solid-phase synthesis. In a preferred embodiment, the B-chain is solubilized in urea.

In a preferred embodiment, the pharmaceutical composition is a vaccine.

Higher ratios of TGF-β1 concentration in the supernatant of the B chain stimulated/unstimulated cells of the T cell stimulation assay were found at week 4 and 12 (p=0.03 and 0.02, respectively, FIG. 4) in the B-chain vaccinated group compared to the placebo group. No other significant differences were detected in the cytokine production (IL-10, IL-17, IL-4, IFN-gamma) of the cell cultures between the arms.

iNKT cell frequencies were monitored in peripheral blood (K is et al., J Leukoc. Biol 81:654-662 (2007)) as follows. Approximately 9 million PBMCs were thawed, washed in phosphate buffered saline (PBS, pH:7.4) and stained with FITC-labeled anti-6B11 antibody (1:20 dilution; BD Biosciences Pharmingen, San Diego, Calif.) and PE-labeled anti-Vα4 antibody (1:50 dilution; Coulter, Marseille, France), in a staining medium of PBS and 0.5% heat-inactivated human AB serum, on ice for 30 minutes. Following washing with PBS, the cells were resuspended in 0.5 ml fixing medium (2% formalin in PBS) and the frequency of double positive cells was measured by a Beckman Coulter XL FACS analyzer.

The mean percentage value of iNKT cells doubled in the insulin B-chain vaccinated group (from 0.047 to 0.085% of total lymphocytes) and from week 4 and afterwards, this increase was sustained compared to the placebo group, however these differences did not reach the level of significance.

Example 3: Diabetes Autoantibodies

Following vaccination as described in Example 1, levels of autoantibodies specific for diabetes-related autoantigens were evaluated in the vaccinated subjects.

Insulin autoantibody levels were determined as follows. A competitive liquid phase radioimmunoassay was used according to a previously published method (see Vardi et al., Diabetes 36:1286-1291 (1987)). Briefly, 150 µl of serum with 50 µl of 0.04 M phosphosaline buffer is incubated with another set of serum incubated with 50 µl of the same buffer containing human insulin at a concentration of $9 \times 10^6$ nU/ml of buffer. Two hundred µl of human recombinant $^{125}$I labeled insulin (Amersham, GE Healthcare) in a concentration of 7500 nU/ml phosphosaline buffer is added to all tubes for a 7-day incubation. Antibody-bound insulin is precipitated and counted for 10 minutes in a gamma counter (Cobra II Auto-gamma Counter, PerkinElmer Inc. (Packard)). All samples were tested in duplicate with a cut-point used of 39 nU/ml (mean±2 SD); based on the 2005 Diabetes Antibody Standardization Program (DASP), the assay had 46% sensitivity and 96% specificity (Tom et al., Diabetologia 51:846-852 (2008)). For Insulin isotyping, the same competitive assay method was performed using 96 well format plates, with biotin-labeled mouse mAb against human IgG1, IgG2, IgG3, IgG4, IgE, or, as a control for non-specific binding, against rat IgM (Pharmingen), used to precipitate isotype specific immune complexes (6.3 µl serum/each isotype measurement).

IA2 and GAD65 autoantibody assays were evaluated using radioimmunoassay performed according to the method of Grubin et al. (Diabetologia 37:344-350 (1994)) and Payton et al. (JCI 96:1506-1511. (1995)), respectively. Briefly, serum samples and negative and positive control samples were incubated with [$^{35}$S]methionine-labeled GAD65 or IA2 containing buffer. The next day, 50-µl aliquots of the serum samples were incubated on coated Millipore plates with protein A-sepharose CL-4B beads (Amersham, GE Healthcare). Scintillation liquid (Optiphase Supermix, Perkin Elmer Inc.) was added to each well and cpm values were measured. All samples were tested in triplicate. Results are expressed in indices (positive control cpm-sample cpm/positive control cpm-negative control cpm). The cut-point used was 0.1 for both assays (mean±2SD); as per the 2007 DASP, the GAD65 and IA2 assays had sensitivity/specificity of 80%/99% and 76%/99%, respectively.

A significant and sustained immune response was observed in all vaccine-treated subjects after only a single dose of insulin B-chain vaccine. Insulin B-chain-specific antibodies (IAA) were significantly higher in the vaccinated group. The low levels of insulin antibody in the placebo group result from exposure to daily subcutaneous insulin. Antibody levels in the vaccinated group slowly decreased over time and eventually approached baseline levels (FIG. 4).

As seen in FIG. 4, insulin auto-antibodies (IAA) were higher in the treatment group than in the control group with p values of 0.069, 0.030 and 0.068 at 8, 12 and 24 weeks, respectively. The induced insulin antibody response decreased slowly over time until it was comparable with that of controls between 78 and 104 weeks. Control subjects demonstrated a small increase in insulin antibodies, reaching a plateau after 8 weeks, and attributable to daily injections of s.c. insulin throughout the study. No differences were seen between the treatment and control groups for IA2 and GAD65 autoantibodies (other islet cell auto-antigens) throughout the study.

These data are consistent with the specific induction of insulin B chain antibodies in response to the insulin B chain vaccination, contributing to the insulin autoantibodies, with induced antibody titers falling over time as expected in the absence of a vaccine booster dose. The duration of the immune response may be attributable to a depot effect from the water-in-oil emulsion adjuvant. Importantly, the reversibility of the induced antibody response to insulin and the lack of change in antibody response to other islet cell antigens, IA2 and GAD, suggest that vaccination with insulin B chain in IFA was both specific and reversible for the immunizing antigen, with no exacerbation of autoimmunity.

Example 4: Clinical Parameters of Diabetes in Vaccinated Subjects

A number of clinical parameters were evaluated over time in the subjects described in Example 1. CBCs with differentials, complete laboratory chemistries (including liver and kidney function tests) and urine analyses were performed at follow-up visits scheduled at weeks 1, 2, 3, 4, 8, 12, 24, 52, 78 and 104 post-treatment. At baseline, and then at weeks 4, 12, 24, 52, 78 and 104, 100 ml of heparinized blood was collected from each patient. Metabolic controls were assessed by recording insulin dose, HbA1c measurements and stimulated C-peptide values using mixed meal tolerance test [MMTT] (Schatz et al., Pediatr Diabetes 5:72-79 (2004)) at entry and at weeks 12, 24, 52, 78 and 104. The primary endpoint of the study was safety, assessed by clinical endpoints including adverse events, local reactions, detailed physical exams, insulin dose, and laboratory tests. Secondary endpoints included immune responses to the vaccination, both humoral and cellular.

Figure 5:
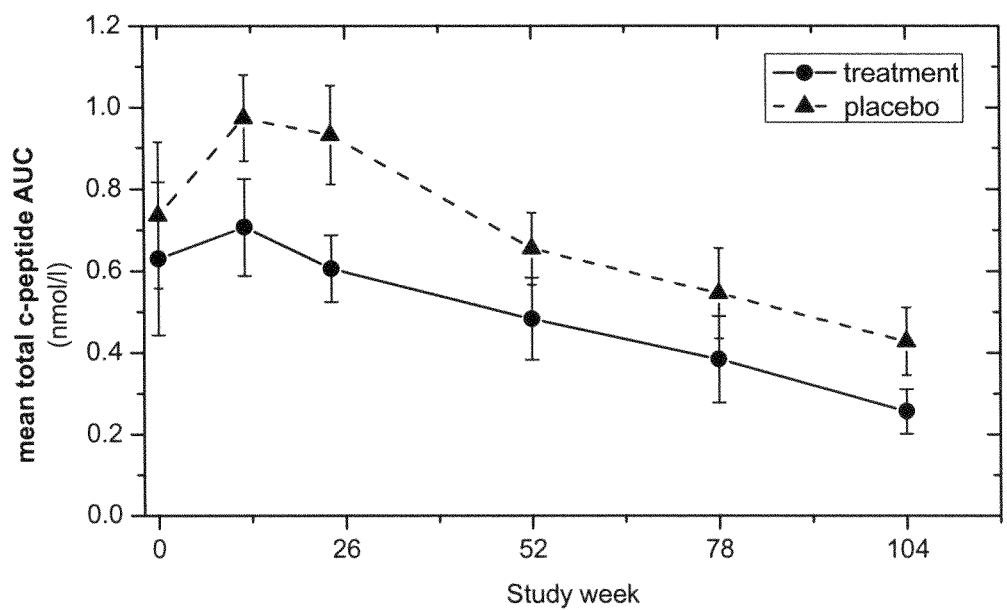
FIG. 5 is a line graph showing mean total C-peptide area under the curve (AUC) for the mixed meal tolerance test (MMTT) by group over time.

The mean total C-peptide AUC responses, a marker for Self-insulin production (beta cell function), were evaluated following a 2 hour Mixed Mean Tolerance Test (MMTT) using standard methods. The results showed a significant decline in both groups over time (p=0.027) (FIG. 5). However, there was no statistical difference between the drug-treated (IBC-VS01) and placebo (VS02) groups. Four out of six subjects with the lowest stimulated C-peptide (mean total C-peptide AUC<0.5 nmol/l) were randomized to the insulin B-chain vaccinated group. Even though after 3 months the stimulated C-peptide values declined in both groups, the slope of decline showed a more favorable trend in the insulin B-chain vaccinated group (x∓SEM).

T cell SI were determined as described above and the two measures were compared. Using standard statistical analysis methods, there was a correlation value of R=0.78, which is a positive correlation. These results indicate that insulin B chain vaccinated individuals exhibited a regulatory T cell response that was associated with better preservation of self insulin production.

Figure 6:
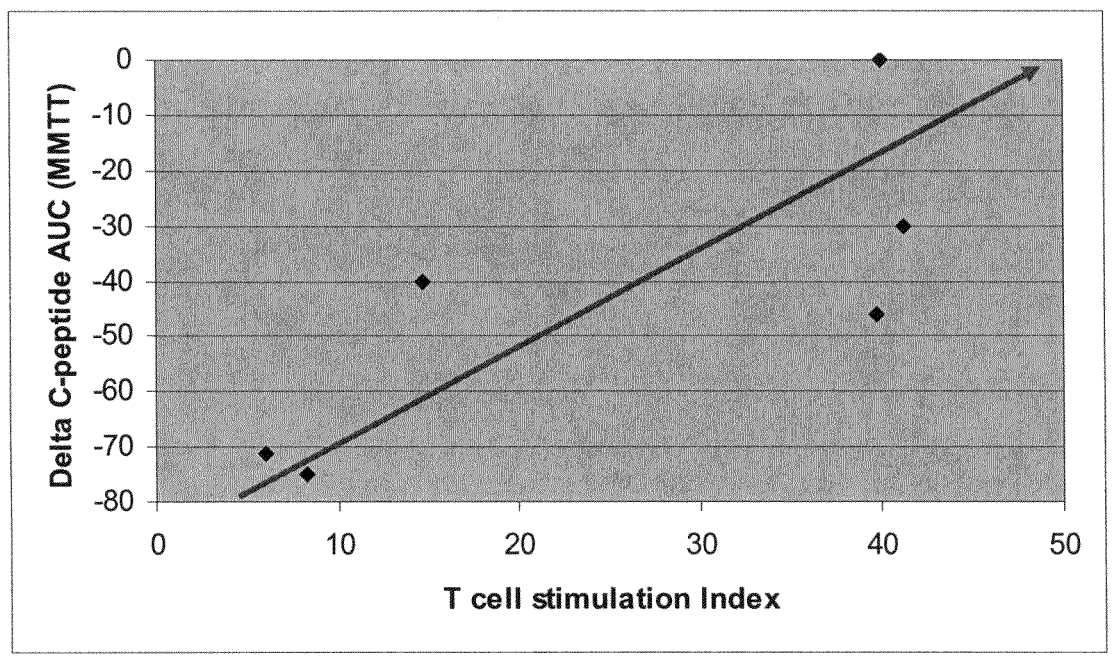
FIG. 6 is a line graphs showing C-peptide AUC change in vaccinated patients plotted against the T cell stimulation index (SI). Correlation: R=0.78

A strong positive correlation was observed between the target antigen-specific T cell proliferative response and residual C-peptide, an endogenous marker for islet cell functionality (FIG. 6). Moreover, two vaccinated patients with the lowest islet cell functionality, and concomitantly the highest daily insulin requirements upon entry into the study, demonstrated reduced daily insulin requirements which fell to remission levels (≤0.25 U/kg) over the 12 weeks immediately following vaccination with insulin B-chain. This corresponded with the rise in the immune response which also peaked at 12 weeks. Their daily insulin requirement remained at remission levels throughout the remainder of the study.

Hemoglobin A1c levels, assayed using standard methods, showed a rapid decline in both groups over the first 12 weeks. The HbA1c values were numerically higher in the treatment group, but were not significantly different from the placebo control group. The HbA1c values for all patients were within the ADA guidelines by 3 months demonstrating that the patients' disease was in good control and not exacerbated by the treatment.

The daily insulin use (U/kg body weight) in the treatment group increased initially over the first 4 weeks, but then dropped from week 4 to 24. The daily insulin dose was significantly higher in the treatment group at week 3 (p=0.026) and week 4 (p=0.041). The overall rate of decline in insulin use for the treatment group was more rapid than for the control group (p=0.012 for the difference between the slopes). The overall daily insulin dose, however, does not differ significantly between groups (p=0.094). The actual insulin usage between weeks 24 and 78 was approximately 0.25 U/kg in both groups indicating that the patients were in remission.

The subjects enrolled in the study were patients with newly diagnosed T1DM whose disease during follow up was in good control. The response of the surrogate marker for β cell function and assessment of their clinical status by HbA1c and daily insulin usage are consistent with this observation. The patients' HbA1c within the recommended targeted range by current ADA guidelines and insulin usage between 24 and 78 weeks at approximately 0.25 IU/kg in both groups indicates that these study subjects were in remission.

Though exposure of the subjects was limited to a single dose of the vaccine and the patient numbers were relatively few, so that differentiation based upon clinical benefit could not be assessed, there was a clear immunological differentiation, both cellular and humoral, of the treated patients compared to those who received placebo, and a demonstration of the specificity and reversibility of the immune response towards the insulin B chain in IFA. The insulin B chain in IFA was safe and very well tolerated.

These results indicate that vaccination with the insulin B-chain was highly efficient, specific for the immunizing antigen, reversible, and did not break immune self tolerance or exacerbate autoimmunity towards other islet cell autoantigens. In addition, as noted above, all patients vaccinated with insulin B-chain (IBC-VS01) gave a marked antigen-specific T cell proliferative response (SI), while placebo treated patients (VS02) did not (FIG. 1). Significantly, the T cell proliferative response was highly specific for the immunizing antigen. Insulin B chain truncated analogs such as B:9-23 and B5-20 peptides, sequences reportedly spanning an immunologically dominant region of the insulin B chain, as well as the insulin precursor pro-insulin, all induced less robust T cell proliferation as compared to the native insulin B chain (Table 1). This confirms that the antigen in the vaccine should as closely as possible match the intact native B chain of insulin, insulin being the only islet cell-specific autoantigen, and a dominant autoantigen expressed early during disease progression. Results, using HLA matched insulin B chain tetramers to select and clone the responder T cells, showed that these clones are $CD4^+$, $CD25^+$ and $CR45RO^+$ and express Foxp3, and the regulatory cytokines TGF-beta and IL-10, characteristics consistent with a regulatory T cell phenotype (Table 2). In addition, mixed peripheral blood T cells from vaccinated patients expressed statistically significant levels of the regulatory cytokine TGF-β upon stimulation with the target antigen.

These results indicated that a clear insulin-specific humoral response was elicited by the treatment. IAA levels, which peaked at 12 weeks then gradually declined, were significantly higher compared to placebo at weeks 8, 12, and 24. Although some elevation of IAA values was noted in the placebo-vaccinated patients, these values stayed within the range typical of subjects receiving exogenous insulin to control diabetes (Fineberg et al., Endocr. Rev. 28:625-652 (2007)). The increased IAA levels cannot be attributed to differences in insulin dose, as both arms reported similar doses throughout the study.

Example 5: Isolation of B-Chain Specific T-Cell Clones

Single cell T cell clones were isolated and expanded from the two subjects' specimens that had the strongest B-chain-specific T cell responses. Cloning attempts on cells from subjects with no B-chain-specific T cell response did not yield clones.

PBMC were isolated from the subjects described in Example 1 and stimulated with 100 ug/ml. of the B chain peptide in cRPMI for 7 days. (Unstimulated PBMC were used as negative controls.) The cells were then stained for 4 hours at 37° C. with HLA identical tetramers, empty or loaded with antigen. The construction of the expression vectors for generation of soluble DR0401 (DPA*0101/DRB1*0401), DR0101 (DRA1*0101/DRB1*0101) or DR0301 (DRA1*0101/DRB1*0301) tetramer molecules has been described previously (Novak et al., J Clin Invest 104:R63-R67 (1999)).

Single cell sorting was then used to isolate those cells bound to the HLA tetramers. The cells were then cultured on allogeneic feeders cells, with IL-2 and PHA for 8-14 days until $10^6$-$10^7$ cells were present. An antigen stimulation assay as described in Example 2 was then conducted to confirm the specificity of the T cells.

After 8 days of prestimulation with the specific antigens, as per methods described above for the T cell stimulation assay, cells were removed from culture, washed and resuspended in 100 μl culture medium containing 10% human AB serum, then split into two 5 ml polystyrene tubes. Next, 1 μL peptide-loaded PE-labeled HLA-matched tetramers are added (empty HLA-matched tetramer is used as negative control) and incubated for 4 hours at 37° C., followed by an incubation with FITC-labeled anti-CD4 antibody (BD Biosciences PharMingen, USA) on ice for 30 minutes.

A carboxyfluorescein diacetate succinimidyl ester (CFSE) assay was performed to analyze the effector functions of T cells. PBMCs were incubated at 37° C. for 5 minutes with 0.5 μM CFSE (stock at 0.5 mM in DMSO, Invitrogen, USA). Staining was terminated by adding cRPMI, the cells are washed, resuspended in culture medium and cultured in 96-well plates, as in the T cell stimulation assay, with medium alone, TT (0.1 LfU/ml) or insulin B chain (50 μg/ml). After 7 days of culture, the cells are washed and stained on ice with anti-CD4-PE antibody (BD Biosciences PharMingen, USA) for 30 minutes. Prior to sorting propidium iodide viability staining is applied (Mannering et al., J Clin Invest 104:R63-R67 (2005)).

The double positive cells from the tetramer staining and propidium-iodide negative, CD4+, CFSEdim cells from the CFSE assay are single cell sorted using a BD FACS Aria cell sorter into the inner 60 wells of 96-well, round bottom, polystyrene plates with each well containing 150,000 irradiated (5000 rad) allogenic feeder cells, 3 μg/ml phytohaemagglutinin (Remel Inc., USA) and 20 U/ml IL-2 in 200 μl culture medium. The outside wells contained 200 μl PBS. Every second day, 100 μl medium Was replaced with fresh medium containing 20 U/ml IL-2 for the tetramer stained cells; in the case of CFSE-stained cells, each week 100 μl medium is replaced with fresh medium containing 20 U/ml IL-2 and 5 ng/ml IL-4. After 2 weeks, the wells were screened for growth and growing clones are expanded.

To confirm antigen specificity, clones are stained with the original PE labeled antigen-loaded tetramer and FITC labeled anti-CD4 antibody.

Antigen-specific clones thus identified were analyzed using FACS (see FIGS. 7A-D and 8A-B), PCR/sequencing, and ELISA for the following antigens: CD25, CD4, CD45RO, Foxp3, TGFβ, IL-10, IL-4, INF-γ.

The clones were confirmed and identified using an antigen stimulation assay. Briefly, the cells were left without any stimulation for at least 3 days. The same patient's PBMCs were incubated with the specific antigen, with tetanus toxoid and without antigen for 2 hours; they were then irradiated (2000 rad), washed, and placed into 96-well plates at a density of 100,000 cells/well using at least 2 wells for each condition. Additional antigens were added to the corresponding conditions and 50,000 cells from the clones are added to the wells. On the 7th day supernatant was collected for cytokine assessment and the cells are treated with 1 μCi/well $^3$H-thymidine for overnight. The next day $^3$H-thymidine incorporation was assessed and the stimulation index was calculated (as above).

Figure 10:
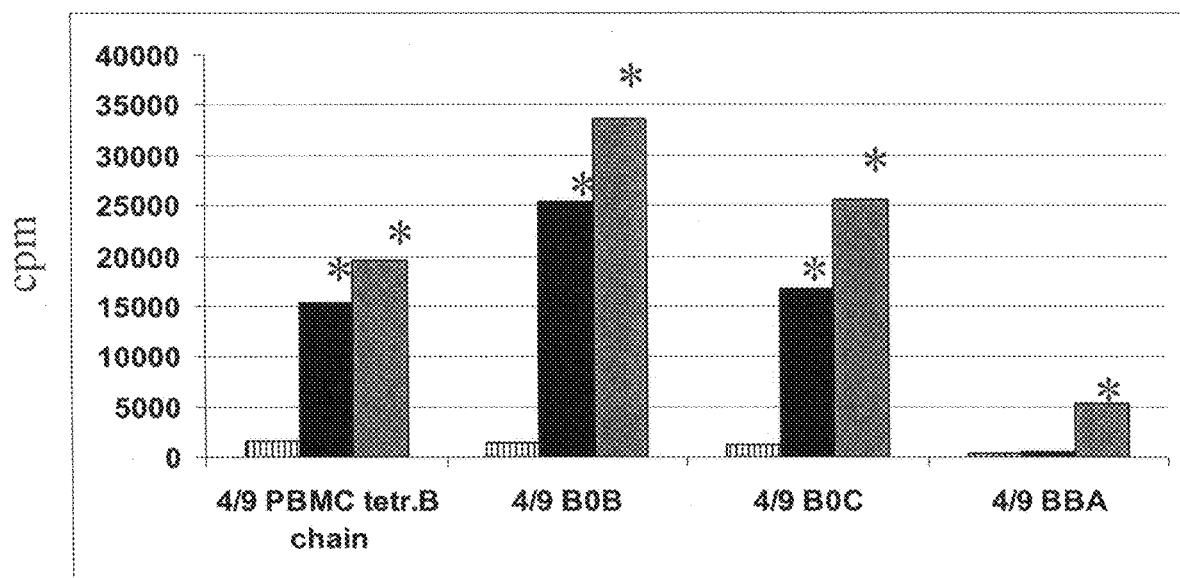
FIG. 10 is a bar graph showing the dose dependent activation of the clones, after stimulation without antigen (striped bar), with low dose B chain (50 ug/ml, black bar) and high dose B chain (100 ug/ml, gray bar). *p<0.05

The SI of the clones was evaluated after stimulation without antigen, with B chain and Tetanus toxoid (see FIG. 9, *p<0.05). Dose dependent activation of the clones was also determined; the clones were stimulated without antigen, low dose B chain (50 ug/ml) and high dose B chain (100 ug/ml) (see FIG. 10, *p<0.05).

Interleukin-10 (IL-10) production was measured with Human IL-10 ELISA kit (eBioscience, USA), TGF-beta with the Human TGF-beta1 DuoSet (R&D Systems, USA) according to the manufacturers' protocols.

PCR analysis of TGF-beta, FoxP3, and TCR expression was carried our as follows. RNA extraction was performed using RNAEasy Microkit® (Qiagen, Germany) according to the manufacturer's protocol (including DNase digestion). Matrix bound RNA is re-suspended in DEPC-treated water, and quantified at 260 nm. The cDNA was produced from the total RNA with reverse transcriptase with random hexamers following the manufacturer's protocol (Invitrogen, USA). Primers were designed and PCR was performed on the cDNA using Platinum® Taq DNA polymerase (Invitrogen, USA) in 25 μl reactions according to the manufacturer's protocol. GAPDH or beta-2 microglobulin is used as a housekeeping gene. DNA templates were recovered from PCR products with a QIAquick™ PCR purification kit (Qiagen, Germany). Templates were sequenced with an ABI3100 Analyzer from both sides with forward and reverse primers.

Four autoantigen specific (insulin B-chain) human CD4+ T cell clones have been isolated and characterized, as described in Table 2.

TABLE 2

Isolated T-Cell Clones

| Method | 4/9 PBMC direct B-chain tetramer sort | 4/9 B chain stimulated cell culture, then B chain tetramer sort | 4/9 B chain stimulated cell culture, then B chain tetramer sort | 4/9 B chain 2x stimulated cell culture, then B chain tetramer sort |
|---|---|---|---|---|
| Best B-chain SI | SI: 13 | SI: 24 | SI: 20 | SI: 19 |
| Name of the clone | PBMC C | B0 B | B0 C | BB A |
| Surface markers | CD4+, CD25+, CD45Ro+ | CD4+, CD25+, CD45Ro+ | CD4+, CD25+, CD45Ro+ | CD4+, CD25+, CD45Ro+ |
| Foxp3 with stains/PCR sequencing | Foxp3+ | Foxp3+ | Foxp3+ | Foxp3+ |
| TGFβ with stains/PCR sequencing | TGFβ+ | TGFβ+ | TGFβ+ | TGFβ+ |
| IL-10 (pg/ml) after CD3 and B-chain stimulation, by ELISA | 552/3.34 | 1213/8.2 | 0.035/17.3 | <0.078 |

To assess the suppressive capacity of the clones an APC-free suppression assay system was used (Oberg et al., Scand. J Immunol 64:353-360 (2006)). T cell Activation/Expansion Beads (Miltenyi Biotec) were coated with anti-CD2, anti-CD3 and anti-CD28 monoclonal antibodies (5 μg/ml) according to the manufacturer's protocol. Responder (CD4+ CD25−) T cells were sorted from the same subject and 10,000 cells are stimulated with 20,000 coated beads alone or with different numbers of cells from the single cell clones (10,000, 5,000, 2500; i.e. cell ratios: 1:1, 1:1/2, 1:1/4). Also, 10,000 cells from the clones were stimulated with the beads without responder T cells. The cells were cultured for 5 days and then are treated with 1 μCi/well 3H-thymidine for overnight. The next day 3H-thymidine incorporation was assessed. The level of inhibition is expressed as percentage value (100−[cpm of the 1:1 ratio divided by the cpm value of the responder T cells×100]).

Intracellular FoxP3 staining was evaluated using a FITC labeled anti-human Foxp3 Staining Set (eBioscience, USA) according to the manufacturer's protocol.

Figure 12:
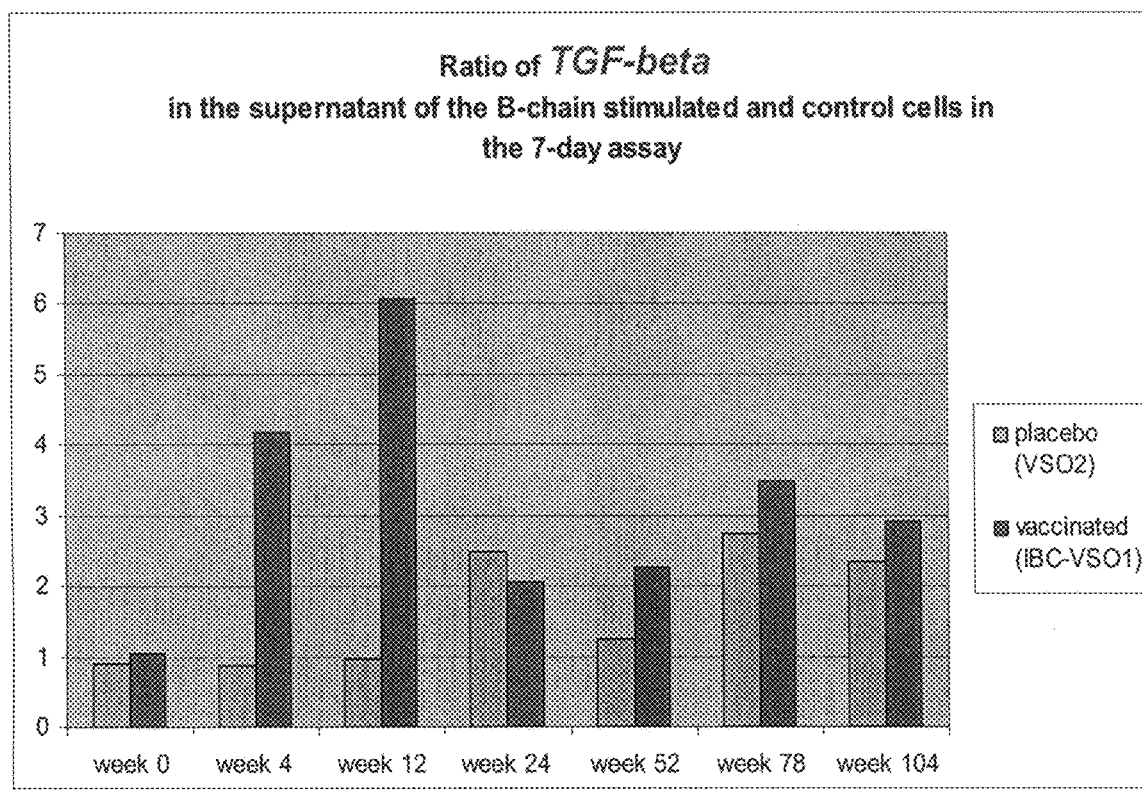
FIG. 12 is a bar graph showing the ratio of the chemokine, TGF-beta in the supernatant of the B-chain stimulated (insulin B-chain vaccinated patients, IBC-VS01) and control cells (placebo vaccinated patients, VS02) in the 7-day assay measured by ELISA. Higher rates were found at weeks 4 and 12 (p=0.03 and 0.02 respectively).

All clones have the same phenotype, and have all the key characteristics of regulatory T cells (see Table 3). These cells have the capacity to "home" to the islet (recognizing the insulin B-chain) and release regulatory cytokines, including IL-10 and TGF-beta (see FIG. 12) and perform cell to cell regulatory functions; they inhibit CD4+/CD25− naïve effector cell expansion (see Table 4).

TABLE 3

Regulatory Phenotype Insulin B-Chain Specific Clones

Total Number of clones: 37

| | Number Tested | Number Confirmed | Confirmed % |
|---|---|---|---|
| CD4 +ve | 37 | 37 | 100.0 |
| CD45RO +ve | 35 | 35 | 100.0 |
| FOXP3/FACS (pos > 23%) | 15 | 12 | 80.0 |
| CD127 −ve | 31 | 34 | 100.0 |
| Colonal expansion to insulin B-chain (pos: SI > 3) | 37 | 14 | 37.8 |

TABLE 3-continued

Regulatory Phenotype Insulin B-Chain Specific Clones

Total Number of clones: 37

| | Number Tested | Number Confirmed | Confirmed % |
|---|---|---|---|
| FOXP3/PCR +ve | 31 | 27 | 87.0 |
| TGFbeta PCR +ve | 26 | 26 | 100.0 |

TABLE 4

Inhibitory Capacity of Insulin B-chain Specific Regulatory T Cell Clones.

| | Characteristics of the two inhibitory clones | |
|---|---|---|
| Clone | Z* | AA* |
| CD4 | Pos | Pos |
| CD45RO | Pos | Pos |
| FOXP3/FACS (pos > 23%) | 31% | 31% |
| CD127 | Neg | Neg |
| Colonal expansion to insulin B-chain (pos: SI > 3) | NSP | NSP |
| FOXP3/PCR | Pos | Pos |
| TGFbeta PCR | Pos | Pos |
| TGF beta secretion | Yes | No |
| IL-10 secretion | No | Yes |
| Level of inhibition at the 1:1 Reg: T responder ratio | *no % | **32% |

NSP = No Significant Proliferation

Figure 11:
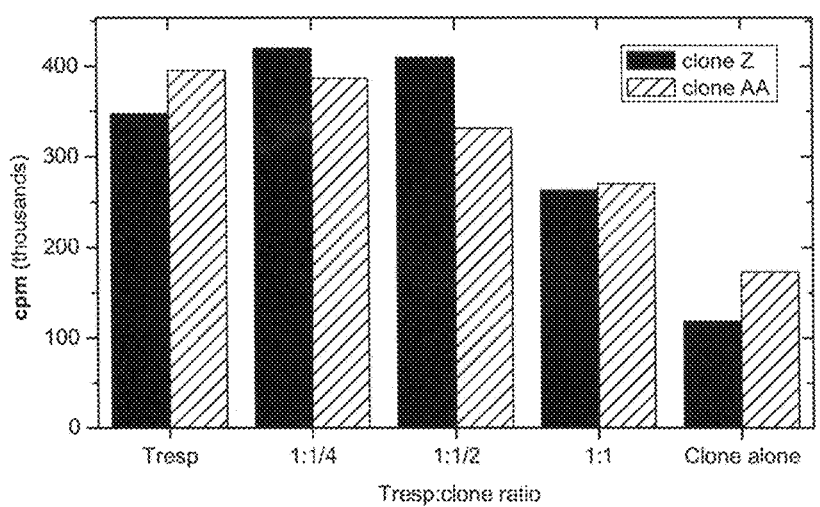
FIG. 11 is a graph of the results of a suppression assay of two. CFSE-B-chain single cell clones with different cell-to-cell ratios of the CD4+CD25− (responder T, 10000) cells and the cells from the clones (2500-5000-10000) of the same subject. The cells were stimulated with bead bound anti-CD-2, anti-CD3 and anti-CD28 (5 μg/ml, Miltenyi Biotec). Responder T cells and cells from the clones were stimulated alone, also. Tritium labeled thymidine (H3 Thymidine) incorporation was assessed after 5 days of culturing. Due to limited cell numbers the cocultures were put together without replicates.

Thus all of the clones obtained exhibited one or more phenotypic markers of regulatory T cells. Two clones exhibited sufficient cell growth to permit functional assays as well (Z and AA; Table 4) and demonstrated suppressive capacity in the T cell suppression assay with 20 and 32% inhibition, as illustrated in FIG. 11. Further characterization of these cells by measurement of IL-10 and TGF-beta1 in the supernatants from the inhibition assays revealed that clone Z produced TGF-beta1 upon stimulation (34 pg/ml in the supernatant of the cells with 1:1 ratio in the functional assay), but no IL-10; clone AA produced IL-10 (188 pg/ml in the supernatant of the cells with 1:1 ratio in the functional assay), but not TGF-beta1.

In order to assess the polyclonality of the clones, T cell receptor alpha and beta chains were sequenced for the insulin B-chain tetramer positive CD4+ T-cell clones. Briefly, total RNA is isolated from CD4+ T-cell clones using an RNeasy Mini Kit (Qiagen) and cDNA is synthesized with a Taqman Reverse Transcription Kit (Applied Biosystems). A set of five multiplex PCR reactions covering a majority of the human V-beta repertoire are performed as per Akatsuka et al. (Tissue Antigens. 53:122-134 (1999)) and two series of amplifications, first, with pooled V-alpha primers and then, with specific V-alpha primers covering the CDR3 regions, are performed as per Seitz et al. (Proc Natl. Acad Sci U.S.A. 103:12057-12062 (2006)). PCR-products are visualized on an ethidium bromide stained 2% agarose gel, sequenced using a Big Dye Terminator v1.1 Cycle Sequencing Kit (Applied Biosystems) with either a TCR constant region 3' primer or a specific variable region 5' primer, and then run on an ABI3100 Genetic Analyzer. TCR alpha and beta CDR3 sequence data are analyzed using the IMGT/V-QUEST web-based program (imgt.cines.fr) from the Universite Montpellier, France (Giudicelli et al., Nucleic Acids Res. 32:W435-W440 (2004)). The CDR3 regions in each were found to be different, indicating that each of the clones was unique (Table 3).

TABLE 3

CDR3 sequences of the TCR alpha and beta chains from four B-chain specific CD4+ T-cell clones. The TCR alpha and beta chain CDR3 sequences of four CD4+ T-cell clones specific for the insulin B-chain were analyzed.

| Clones | Alpha CDR3 | | Beta CDR3 | | |
|---|---|---|---|---|---|
| BB | | | TRBV29-1 TRBJ1-2 | TRBD1*01 | CSVHSGDGGYTF (SEQ ID NO: 7) |
| BC | TRAV39 TRAJ58 | CASRETSGSRLTF (SEQ ID NO: 8) | TRBV11-2 TRBJ2-2 | TRBD2*02 | CASREGVLRPTGELFF (SEQ ID NO: 9) |
| BD | | | TRBV20-1 TRBJ2-5 | TRBD2*01 | CSAGRGGALETQYF (SEQ ID NO: 10) |
| BOB | TRAV35 TRAV40 | CAGREDSGTYKYIF (SEQ ID NO: 11) | TRBV4-1 TRBJ2-5 | TRBD2*01 | CASSRSGAGAQETQYF (SEQ ID NO: 12) |

To test whether the cloning procedure itself could produce regulatory T cells, FACS-sorted CD4+ CD25− T cells from both healthy controls and T1DM patients were subject to the same cloning and expansion process. No regulatory T cells were induced; the cells remained CD127 positive and Foxp3 negative by FACS analysis, and functional assays showed no inhibition.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject for the development or progression of autoimmune diabetes comprising:
    obtaining a blood sample from the subject:
    detecting whether insulin autoantigen specific CD8+ cytotoxic T cells are present in the blood sample:
    diagnosing the subject as susceptible to the development or progression of autoimmune diabetes when the presence of insulin autoantigen specific CD8+ cytotoxic T cells are detected in the blood sample:
    treating the diagnosed subject by parenterally administering to the subject an effective amount of a therapeutic composition comprising insulin β-chain autoantigen in a water-in-oil adjuvant emulsion comprising mannide monooleate, polyoxyl-40-hydrogenated castor oil, squalene and squalane sufficient to stimulate insulin β-chain autoantigen-specific CD4+, CD25+, Foxp3+ regulatory T cells in the subject;
    obtaining additional blood samples from the treated subject:
    detecting the presence of insulin β-chain autoantigen specific CD4+, CD25+, Foxp3+ regulatory T cells (Tregs) in the additional blood samples of the treated subject; and
    parenterally administering one or more subsequent doses of the therapeutic composition sufficient to suppress the function of insulin autoantibody specific CD8+ cytotoxic T cells in the treated subject.

2. A method of treating a mammalian subject to prevent the progression of an autoimmune disease comprising:
    obtaining a blood sample from the subject:
    detecting the presence of autoantigen specific cytotoxic CD8+ T cells in the subject, wherein the autoantigen is associated with the autoimmune disease in the subject;
    diagnosing the subject as susceptible to the autoimmune disease when the presence of auto autoantigen specific cytotoxic CD8+ T cells are detected in the blood sample;
    treating the diagnosed subject with an effective amount of a therapeutic composition comprising at least one autoantigen associated with the autoimmune disease in a water-in-oil emulsion comprising mannide monooleate, polyoxyl-40-hydrogenated castor oil, squalene and squalane sufficient to induce regulatory T cells specific to the autoantigen in the subject to create a treated subject;
    obtaining additional blood samples from the treated subject:
    detecting the presence of autoantigen-specific CD4+, CD25+, Foxp3+ regulatory T cells in the additional blood samples of the treated subject; and
    parenterally administering a booster amount of the therapeutic composition to the treated subject sufficient to suppress the function of autoantigen specific CD8+ cytotoxic T cells in the treated subject.

3. The method of claim 2, wherein the subject is a human, the autoimmune disease is diabetes, and the autoantigen is insulin B chain.

4. The method of claim 3 wherein the regulatory T cells secrete IL-10, TGF-Beta, or both IL-10 and TGF-Beta.

5. The method of claim 2, wherein the autoimmune disease is diabetes and the autoantigen is GAD65.

6. The method of claim 1 wherein the autoantigen is contained in aqueous globules and the aqueous globules have median diameters in the range from about 100 nanometers to about 1 micron.

7. The method of claim 6 wherein the aqueous globules have an average diameter of about 300 nanometers.

8. A method of treating a subject to inhibit the development or progression of autoimmune diabetes comprising:
    obtaining a blood sample from the subject;
    detecting whether insulin autoantigen specific CD8+ cytotoxic T cells are present in the blood sample;
    diagnosing the subject as susceptible to the development or progression of autoimmune diabetes when the presence of insulin autoantigen specific CD8+ cytotoxic T cells are detected in the blood sample;
    treating the diagnosed subject by parenterally administering to the subject an effective amount of a therapeutic composition comprising insulin β-chain autoantigen in a water-in-oil adjuvant emulsion comprising mannide monooleate, polyoxyl-40-hydrogenated castor oil, squalene and squalane sufficient to stimulate insulin β-chain autoantigen-specific CD4+, CD25+, Foxp3+ regulatory T cells in the subject;
    obtaining additional blood samples from the treated subject;
    detecting the presence of insulin autoantibody specific CD8+ cytotoxic T cells in the additional blood samples of the treated subject; and
    parenterally administering one or more subsequent doses of the therapeutic composition sufficient to suppress the function of insulin autoantibody specific CD8+ cytotoxic T cells in the treated subject.

9. The method of claim 2 or 8, wherein the autoantigen is contained in aqueous globules and the aqueous globules have median diameters in the range from about 100 nanometers to about 1 micron.

10. The method of claim 9 wherein the aqueous globules have an average diameter of about 300 nanometers.

* * * * *

SEQUENCE LISTING

<160> NUMBER OF SEQ ID NOS: 12

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

-continued

Gln Val Glu Leu Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 2
<211> LENGTH: 585
<212> TYPE: PRT
<213> ORGANISM: Homo sapiens

<400> SEQUENCE: 2

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
             340                 345                 350

Ile Cys Lys Lys Tyr Lys Ile Trp Met His Val Asp Ala Ala Trp Gly
             355                 360                 365

Gly Gly Leu Leu Met Ser Arg Lys His Lys Trp Lys Leu Ser Gly Val
             370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Gly Leu Met Gln
             405                 410                 415

Asn Cys Asn Gln Met His Ala Ser Tyr Leu Phe Gln Gln Asp Lys His
             420                 425                 430

Tyr Asp Leu Ser Tyr Asp Thr Gly Asp Lys Ala Leu Gln Cys Gly Arg
             435                 440                 445

His Val Asp Val Phe Lys Leu Trp Leu Met Trp Arg Ala Lys Gly Thr
             450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
             485                 490                 495

Gly Lys Pro Gln His Thr Asn Val Cys Phe Trp Tyr Ile Pro Pro Ser
             500                 505                 510

Leu Arg Thr Leu Glu Asp Asn Glu Glu Arg Met Ser Arg Leu Ser Lys
             515                 520                 525

Val Ala Pro Val Ile Lys Ala Arg Met Met Glu Tyr Gly Thr Thr Met
             530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
             565                 570                 575

Glu Ile Glu Arg Leu Gly Gln Asp Leu
             580                 585

<210> SEQ ID NO 3
<211> LENGTH: 979
<212> TYPE: PRT
<213> ORGANISM: Homo sapiens

<400> SEQUENCE: 3

Met Arg Arg Pro Arg Arg Pro Gly Gly Leu Gly Gly Ser Gly Gly Leu
1               5                   10                  15

Arg Leu Leu Leu Cys Leu Leu Leu Ser Ser Arg Pro Gly Gly Cys
             20                  25                  30

Ser Ala Val Ser Ala His Gly Cys Leu Phe Asp Arg Arg Leu Cys Ser
             35                  40                  45

His Leu Glu Val Cys Ile Gln Asp Gly Leu Phe Gly Gln Cys Gln Val
             50                  55                  60

Gly Val Gly Gln Ala Arg Pro Leu Leu Gln Val Thr Ser Pro Val Leu
65              70                  75                  80

Gln Arg Leu Gln Gly Val Leu Arg Gln Leu Met Ser Gln Gly Leu Ser
             85                  90                  95

Trp His Asp Asp Leu Thr Gln Tyr Val Ile Ser Gln Glu Met Glu Arg
             100                 105                 110

Ile Pro Arg Leu Arg Pro Pro Glu Pro Arg Pro Arg Asp Arg Ser Gly

```
            115                 120                 125
Leu Ala Pro Lys Arg Pro Gly Pro Ala Gly Glu Leu Leu Gln Asp
        130                 135                 140
Ile Pro Thr Gly Ser Ala Pro Ala Gln His Arg Leu Pro Gln Pro
145                 150                 155                 160
Pro Val Gly Lys Gly Gly Ala Gly Ala Ser Ser Leu Ser Pro Leu
                165                 170                 175
Gln Ala Glu Leu Leu Pro Pro Leu Leu Glu His Leu Leu Leu Pro
            180                 185                 190
Gln Pro Pro His Pro Ser Leu Ser Tyr Glu Pro Ala Leu Leu Gln Pro
        195                 200                 205
Tyr Leu Phe His Gln Phe Gly Ser Arg Asp Gly Ser Arg Val Ser Glu
    210                 215                 220
Gly Ser Pro Gly Met Val Ser Val Gly Pro Leu Pro Lys Ala Glu Ala
225                 230                 235                 240
Pro Ala Leu Phe Ser Arg Thr Ala Ser Lys Gly Ile Phe Gly Asp His
                245                 250                 255
Pro Gly His Ser Tyr Gly Asp Leu Pro Gly Pro Ser Pro Ala Gln Leu
            260                 265                 270
Phe Gln Asp Ser Gly Leu Leu Tyr Leu Ala Gln Glu Leu Pro Ala Pro
        275                 280                 285
Ser Arg Ala Arg Val Pro Arg Leu Pro Glu Gln Gly Ser Ser Ser Arg
    290                 295                 300
Ala Glu Asp Ser Pro Glu Gly Tyr Glu Lys Glu Gly Leu Gly Asp Arg
305                 310                 315                 320
Gly Glu Lys Pro Ala Ser Pro Ala Val Gln Pro Asp Ala Ala Leu Gln
                325                 330                 335
Arg Leu Ala Ala Val Leu Ala Gly Tyr Gly Val Glu Leu Arg Gln Leu
            340                 345                 350
Thr Pro Glu Gln Leu Ser Thr Leu Leu Thr Leu Leu Gln Leu Leu Pro
        355                 360                 365
Lys Gly Ala Gly Arg Asn Pro Gly Gly Val Val Asn Val Gly Ala Asp
    370                 375                 380
Ile Lys Lys Thr Met Glu Gly Pro Val Glu Gly Arg Asp Thr Ala Glu
385                 390                 395                 400
Leu Pro Ala Arg Thr Ser Pro Met Pro Gly His Pro Thr Ala Ser Pro
                405                 410                 415
Thr Ser Ser Glu Val Gln Gln Val Pro Ser Pro Val Ser Ser Glu Pro
            420                 425                 430
Pro Lys Ala Ala Arg Pro Pro Val Thr Pro Val Leu Leu Glu Lys Lys
        435                 440                 445
Ser Pro Leu Gly Gln Ser Gln Pro Thr Val Ala Gly Gln Pro Ser Ala
    450                 455                 460
Arg Pro Ala Ala Glu Glu Tyr Gly Tyr Ile Val Thr Asp Gln Lys Pro
465                 470                 475                 480
Leu Ser Leu Ala Ala Gly Val Lys Leu Leu Glu Ile Leu Ala Glu His
                485                 490                 495
Val His Met Ser Ser Gly Ser Phe Ile Asn Ile Ser Val Gly Pro
            500                 505                 510
Ala Leu Thr Phe Arg Ile Arg His Asn Glu Gln Asn Leu Ser Leu Ala
        515                 520                 525
Asp Val Thr Gln Gln Ala Gly Leu Val Lys Ser Glu Leu Glu Ala Gln
    530                 535                 540
```

```
Thr Gly Leu Gln Ile Leu Gln Thr Gly Val Gly Gln Arg Glu Glu Ala
545                 550                 555                 560

Ala Ala Val Leu Pro Gln Thr Ala His Ser Thr Ser Pro Met Arg Ser
                565                 570                 575

Val Leu Leu Thr Leu Val Ala Leu Ala Gly Val Ala Gly Leu Leu Val
            580                 585                 590

Ala Leu Ala Val Ala Leu Cys Val Arg Gln His Ala Arg Gln Gln Asp
        595                 600                 605

Lys Glu Arg Leu Ala Ala Leu Gly Pro Glu Gly Ala His Gly Asp Thr
610                 615                 620

Thr Phe Glu Tyr Gln Asp Leu Cys Arg Gln His Met Ala Thr Lys Ser
625                 630                 635                 640

Leu Phe Asn Arg Ala Glu Gly Pro Pro Glu Pro Ser Arg Val Ser Ser
                645                 650                 655

Val Ser Ser Gln Phe Ser Asp Ala Ala Gln Ala Ser Pro Ser Ser His
            660                 665                 670

Ser Ser Thr Pro Ser Trp Cys Glu Glu Pro Ala Gln Ala Asn Met Asp
        675                 680                 685

Ile Ser Thr Gly His Met Ile Leu Ala Tyr Met Glu Asp His Leu Arg
690                 695                 700

Asn Arg Asp Arg Leu Ala Lys Glu Trp Gln Ala Leu Cys Ala Tyr Gln
705                 710                 715                 720

Ala Glu Pro Asn Thr Cys Ala Thr Ala Gln Gly Glu Gly Asn Ile Lys
                725                 730                 735

Lys Asn Arg His Pro Asp Phe Leu Pro Tyr Asp His Ala Arg Ile Lys
            740                 745                 750

Leu Lys Val Glu Ser Ser Pro Ser Arg Ser Asp Tyr Ile Asn Ala Ser
        755                 760                 765

Pro Ile Ile Glu His Asp Pro Arg Met Pro Ala Tyr Ile Ala Thr Gln
770                 775                 780

Gly Pro Leu Ser His Thr Ile Ala Asp Phe Trp Gln Met Val Trp Glu
785                 790                 795                 800

Ser Gly Cys Thr Val Ile Val Met Leu Thr Pro Leu Val Glu Asp Gly
                805                 810                 815

Val Lys Gln Cys Asp Arg Tyr Trp Pro Asp Glu Gly Ala Ser Leu Tyr
            820                 825                 830

His Val Tyr Glu Val Asn Leu Val Ser Glu His Ile Trp Cys Glu Asp
        835                 840                 845

Phe Leu Val Arg Ser Phe Tyr Leu Lys Asn Val Gln Thr Gln Glu Thr
850                 855                 860

Arg Thr Leu Thr Gln Phe His Phe Leu Ser Trp Pro Ala Glu Gly Thr
865                 870                 875                 880

Pro Ala Ser Thr Arg Pro Leu Leu Asp Phe Arg Arg Lys Val Asn Lys
                885                 890                 895

Cys Tyr Arg Gly Arg Ser Cys Pro Ile Ile Val His Cys Ser Asp Gly
            900                 905                 910

Ala Gly Arg Thr Gly Thr Tyr Ile Leu Ile Asp Met Val Leu Asn Arg
        915                 920                 925

Met Ala Lys Gly Val Lys Glu Ile Asp Ile Ala Ala Thr Leu Glu His
930                 935                 940

Val Arg Asp Gln Arg Pro Gly Leu Val Arg Ser Lys Asp Gln Phe Glu
945                 950                 955                 960
```

```
Phe Ala Leu Thr Ala Val Ala Glu Glu Val Asn Ala Ile Leu Lys Ala
                965                 970                 975

Leu Pro Gln

<210> SEQ ID NO 4
<211> LENGTH: 622
<212> TYPE: PRT
<213> ORGANISM: Homo sapiens

<400> SEQUENCE: 4

Met Ser Met Arg Ser Pro Ile Ser Ala Gln Leu Ala Leu Asp Gly Val
1               5                   10                  15

Gly Thr Met Val Asn Cys Thr Ile Lys Ser Glu Glu Lys Lys Glu Pro
                20                  25                  30

Cys His Glu Ala Pro Gln Gly Ser Ala Thr Ala Ala Glu Pro Gln Pro
            35                  40                  45

Gly Asp Pro Ala Arg Ala Ser Gln Asp Ser Ala Asp Pro Gln Ala Pro
        50                  55                  60

Ala Gln Gly Asn Phe Arg Gly Ser Trp Asp Cys Ser Ser Pro Glu Gly
65                  70                  75                  80

Asn Gly Ser Pro Glu Pro Lys Arg Pro Gly Ala Ser Glu Ala Ala Ser
                85                  90                  95

Gly Ser Gln Glu Lys Leu Asp Phe Asn Arg Asn Leu Lys Glu Val Val
            100                 105                 110

Pro Ala Ile Glu Lys Leu Leu Ser Ser Asp Trp Lys Glu Arg Phe Leu
        115                 120                 125

Gly Arg Asn Ser Met Glu Ala Lys Asp Val Lys Gly Thr Gln Glu Ser
130                 135                 140

Leu Ala Glu Lys Glu Leu Gln Leu Leu Val Met Ile His Gln Leu Ser
145                 150                 155                 160

Thr Leu Arg Asp Gln Leu Leu Thr Ala His Ser Glu Gln Lys Asn Met
                165                 170                 175

Ala Ala Met Leu Phe Glu Lys Gln Gln Gln Met Glu Leu Ala Arg
            180                 185                 190

Gln Gln Gln Glu Gln Ile Ala Lys Gln Gln Gln Leu Ile Gln Gln
        195                 200                 205

Gln His Lys Ile Asn Leu Leu Gln Gln Gln Ile Gln Val Asn Met
210                 215                 220

Pro Tyr Val Met Ile Pro Ala Phe Pro Pro Ser His Gln Pro Leu Pro
225                 230                 235                 240

Val Thr Pro Asp Ser Gln Leu Ala Leu Pro Ile Gln Pro Ile Pro Cys
                245                 250                 255

Lys Pro Val Glu Tyr Pro Leu Gln Leu Leu His Ser Pro Pro Ala Pro
            260                 265                 270

Val Val Lys Arg Pro Gly Ala Met Ala Thr His His Pro Leu Gln Glu
        275                 280                 285

Pro Ser Gln Pro Leu Asn Leu Thr Ala Lys Pro Lys Ala Pro Glu Leu
        290                 295                 300

Pro Asn Thr Ser Ser Ser Pro Ser Leu Lys Met Ser Ser Cys Val Pro
305                 310                 315                 320

Arg Pro Pro Ser His Gly Gly Pro Thr Arg Asp Leu Gln Ser Ser Pro
                325                 330                 335

Pro Ser Leu Pro Leu Gly Phe Leu Gly Glu Gly Asp Ala Val Thr Lys
            340                 345                 350
```

```
Ala Ile Gln Asp Ala Arg Gln Leu His Ser His Ser Gly Ala Leu
        355                 360                 365

Asp Gly Ser Pro Asn Thr Pro Phe Arg Lys Asp Leu Ile Ser Leu Asp
370                 375                 380

Ser Ser Pro Ala Lys Glu Arg Leu Glu Asp Gly Cys Val His Pro Leu
385                 390                 395                 400

Glu Glu Ala Met Leu Ser Cys Asp Met Asp Gly Ser Arg His Phe Pro
                405                 410                 415

Glu Ser Arg Asn Ser Ser His Ile Lys Arg Pro Met Asn Ala Phe Met
            420                 425                 430

Val Trp Ala Lys Asp Glu Arg Arg Lys Ile Leu Gln Ala Phe Pro Asp
        435                 440                 445

Met His Asn Ser Ser Ile Ser Lys Ile Leu Gly Ser Arg Trp Lys Ser
    450                 455                 460

Met Thr Asn Gln Glu Lys Gln Pro Tyr Tyr Glu Glu Gln Ala Arg Leu
465                 470                 475                 480

Ser Arg Gln His Leu Glu Lys Tyr Pro Asp Tyr Lys Tyr Lys Pro Arg
                485                 490                 495

Pro Lys Arg Thr Cys Ile Val Glu Gly Lys Arg Leu Arg Val Gly Glu
            500                 505                 510

Tyr Lys Ala Leu Met Arg Thr Arg Arg Gln Asp Ala Arg Gln Ser Tyr
        515                 520                 525

Val Ile Pro Pro Gln Ala Gly Gln Val Gln Met Ser Ser Asp Val
    530                 535                 540

Leu Tyr Pro Arg Ala Ala Gly Met Pro Leu Ala Gln Pro Leu Val Glu
545                 550                 555                 560

His Tyr Val Pro Arg Ser Leu Asp Pro Asn Met Pro Val Ile Val Asn
                565                 570                 575

Thr Cys Ser Leu Arg Glu Glu Gly Glu Gly Thr Asp Asp Arg His Ser
            580                 585                 590

Val Ala Asp Gly Glu Met Tyr Arg Tyr Ser Glu Asp Glu Asp Ser Glu
        595                 600                 605

Gly Glu Glu Lys Ser Asp Gly Glu Leu Val Val Leu Thr Asp
    610                 615                 620

<210> SEQ ID NO 5
<211> LENGTH: 483
<212> TYPE: PRT
<213> ORGANISM: Homo sapiens

<400> SEQUENCE: 5

Met Ser Gly His Lys Cys Ser Tyr Pro Trp Asp Leu Gln Asp Arg Tyr
1               5                   10                  15

Ala Gln Asp Lys Ser Val Val Asn Lys Met Gln Gln Arg Tyr Trp Glu
                20                  25                  30

Thr Lys Gln Ala Phe Ile Lys Ala Thr Gly Lys Lys Glu Asp Glu His
            35                  40                  45

Val Val Ala Ser Asp Ala Asp Leu Asp Ala Lys Leu Glu Leu Phe His
        50                  55                  60

Ser Ile Gln Arg Thr Cys Leu Asp Leu Ser Lys Ala Ile Val Leu Tyr
65                  70                  75                  80

Gln Lys Arg Ile Cys Phe Leu Ser Gln Glu Glu Asn Glu Leu Gly Lys
                85                  90                  95

Phe Leu Arg Ser Gln Gly Phe Gln Asp Lys Thr Arg Ala Gly Lys Met
            100                 105                 110
```

Met Gln Ala Thr Gly Lys Ala Leu Cys Phe Ser Ser Gln Arg Leu
            115                 120                 125

Ala Leu Arg Asn Pro Leu Cys Arg Phe His Gln Glu Val Glu Thr Phe
        130                 135                 140

Arg His Arg Ala Ile Ser Asp Thr Trp Leu Thr Val Asn Arg Met Glu
145                 150                 155                 160

Gln Cys Arg Thr Glu Tyr Arg Gly Ala Leu Leu Trp Met Lys Asp Val
                165                 170                 175

Ser Gln Glu Leu Asp Pro Asp Leu Tyr Lys Gln Met Glu Lys Phe Arg
            180                 185                 190

Lys Val Gln Thr Gln Val Arg Leu Ala Lys Lys Asn Phe Asp Lys Leu
        195                 200                 205

Lys Met Asp Val Cys Gln Lys Val Asp Leu Leu Gly Ala Ser Arg Cys
210                 215                 220

Asn Leu Leu Ser His Met Leu Ala Thr Tyr Gln Thr Thr Leu Leu His
225                 230                 235                 240

Phe Trp Glu Lys Thr Ser His Thr Met Ala Ala Ile His Glu Ser Phe
                245                 250                 255

Lys Gly Tyr Gln Pro Tyr Glu Phe Thr Thr Leu Lys Ser Leu Gln Asp
            260                 265                 270

Pro Met Lys Lys Leu Val Glu Lys Glu Lys Lys Ile Asn Gln
        275                 280                 285

Gln Glu Ser Thr Asp Ala Ala Val Gln Glu Pro Ser Gln Leu Ile Ser
            290                 295                 300

Leu Glu Glu Glu Asn Gln Arg Lys Glu Ser Ser Phe Lys Thr Glu
305                 310                 315                 320

Asp Gly Lys Ser Ile Leu Ser Ala Leu Asp Lys Gly Ser Thr His Thr
                325                 330                 335

Ala Cys Ser Gly Pro Ile Asp Glu Leu Leu Asp Met Lys Ser Glu Glu
            340                 345                 350

Gly Ala Cys Leu Gly Pro Val Ala Gly Thr Pro Glu Pro Glu Gly Ala
        355                 360                 365

Asp Lys Asp Leu Leu Leu Ser Glu Ile Phe Asn Ala Ser Ser
370                 375                 380

Leu Glu Glu Gly Glu Phe Ser Lys Glu Trp Ala Ala Val Phe Gly Asp
385                 390                 395                 400

Gly Gln Val Lys Glu Pro Val Pro Thr Met Ala Leu Gly Glu Pro Asp
                405                 410                 415

Pro Lys Ala Gln Thr Gly Ser Gly Phe Leu Pro Ser Gln Leu Leu Asp
            420                 425                 430

Gln Asn Met Lys Asp Leu Gln Ala Ser Leu Gln Glu Pro Ala Lys Ala
        435                 440                 445

Ala Ser Asp Leu Thr Ala Trp Phe Ser Leu Phe Ala Asp Leu Asp Pro
450                 455                 460

Leu Ser Asn Pro Asp Ala Val Gly Lys Thr Asp Lys Glu His Glu Leu
465                 470                 475                 480

Leu Asn Ala

<210> SEQ ID NO 6
<211> LENGTH: 471
<212> TYPE: PRT
<213> ORGANISM: Homo sapiens

<400> SEQUENCE: 6

-continued

```
Met Ser His His Pro Ser Gly Leu Arg Ala Gly Phe Ser Ser Thr Ser
1               5                   10                  15

Tyr Arg Arg Thr Phe Gly Pro Pro Ser Leu Ser Pro Gly Ala Phe
            20                  25                  30

Ser Tyr Ser Ser Ser Ser Arg Phe Ser Ser Ser Arg Leu Leu Gly Ser
        35                  40                  45

Ala Ser Pro Ser Ser Val Arg Leu Gly Ser Phe Arg Ser Pro Arg
    50                  55                  60

Ala Gly Ala Gly Ala Leu Leu Arg Leu Pro Ser Glu Arg Leu Asp Phe
65                  70                  75                  80

Ser Met Ala Glu Ala Leu Asn Gln Glu Phe Leu Ala Thr Arg Ser Asn
                85                  90                  95

Glu Lys Gln Glu Leu Gln Glu Leu Asn Asp Arg Phe Ala Asn Phe Ile
                100                 105                 110

Glu Lys Val Arg Phe Leu Glu Gln Gln Asn Ala Ala Leu Arg Gly Glu
                115                 120                 125

Leu Ser Gln Ala Arg Gly Gln Glu Pro Ala Arg Ala Asp Gln Leu Cys
    130                 135                 140

Gln Gln Glu Leu Arg Glu Leu Arg Arg Glu Leu Glu Leu Leu Gly Arg
145                 150                 155                 160

Glu Arg Asp Arg Val Gln Val Glu Arg Asp Gly Leu Ala Glu Asp Leu
                165                 170                 175

Ala Ala Leu Lys Gln Arg Leu Glu Glu Glu Thr Arg Lys Arg Glu Asp
                180                 185                 190

Ala Glu His Asn Leu Val Leu Phe Arg Lys Asp Val Asp Asp Ala Thr
        195                 200                 205

Leu Ser Arg Leu Glu Leu Glu Arg Lys Ile Glu Ser Leu Met Asp Glu
    210                 215                 220

Ile Glu Phe Leu Lys Lys Leu His Glu Glu Glu Leu Arg Asp Leu Gln
225                 230                 235                 240

Val Ser Val Glu Ser Gln Gln Val Gln Gln Val Glu Val Glu Ala Thr
                245                 250                 255

Val Lys Pro Glu Leu Thr Ala Ala Leu Arg Asp Ile Arg Ala Gln Tyr
                260                 265                 270

Glu Ser Ile Ala Ala Lys Asn Leu Gln Glu Ala Glu Glu Trp Tyr Lys
        275                 280                 285

Ser Lys Tyr Ala Asp Leu Ser Asp Ala Ala Asn Arg Asn His Glu Ala
    290                 295                 300

Leu Arg Gln Ala Lys Gln Glu Met Asn Glu Ser Arg Arg Gln Ile Gln
305                 310                 315                 320

Ser Leu Thr Cys Glu Val Asp Gly Leu Arg Gly Thr Asn Glu Ala Leu
                325                 330                 335

Leu Arg Gln Leu Arg Glu Leu Glu Glu Gln Phe Ala Leu Glu Ala Gly
                340                 345                 350

Gly Tyr Gln Ala Gly Ala Ala Arg Leu Glu Glu Glu Leu Arg Gln Leu
        355                 360                 365

Lys Glu Glu Met Ala Arg His Leu Arg Glu Tyr Gln Glu Leu Leu Asn
    370                 375                 380

Val Lys Met Ala Leu Asp Ile Glu Ile Ala Thr Tyr Arg Lys Leu Leu
385                 390                 395                 400

Glu Gly Glu Glu Ser Arg Ile Ser Val Pro Val His Ser Phe Ala Ser
                405                 410                 415
```

```
Leu Asn Ile Lys Thr Thr Val Pro Glu Val Glu Pro Pro Gln Asp Ser
            420                 425                 430

His Ser Arg Lys Thr Val Leu Ile Lys Thr Ile Glu Thr Arg Asn Gly
            435                 440                 445

Glu Gln Val Val Thr Glu Ser Gln Lys Glu Gln Arg Ser Glu Leu Asp
            450                 455                 460

Lys Ser Ser Ala His Ser Tyr
465             470

<210> SEQ ID NO 7
<211> LENGTH: 12
<212> TYPE: PRT
<213> ORGANISM: Homo sapiens

<400> SEQUENCE: 7

Cys Ser Val His Ser Gly Asp Gly Gly Tyr Thr Phe
1               5                   10

<210> SEQ ID NO 8
<211> LENGTH: 13
<212> TYPE: PRT
<213> ORGANISM: Homo sapiens

<400> SEQUENCE: 8

Cys Ala Ser Arg Glu Thr Ser Gly Ser Arg Leu Thr Phe
1               5                   10

<210> SEQ ID NO 9
<211> LENGTH: 16
<212> TYPE: PRT
<213> ORGANISM: Homo sapiens

<400> SEQUENCE: 9

Cys Ala Ser Arg Glu Gly Val Leu Arg Pro Thr Gly Glu Leu Phe Phe
1               5                   10                  15

<210> SEQ ID NO 10
<211> LENGTH: 14
<212> TYPE: PRT
<213> ORGANISM: Homo sapiens

<400> SEQUENCE: 10

Cys Ser Ala Gly Arg Gly Gly Ala Leu Glu Thr Gln Tyr Phe
1               5                   10

<210> SEQ ID NO 11
<211> LENGTH: 14
<212> TYPE: PRT
<213> ORGANISM: Homo sapiens

<400> SEQUENCE: 11

Cys Ala Gly Arg Glu Asp Ser Gly Thr Tyr Lys Tyr Ile Phe
1               5                   10

<210> SEQ ID NO 12
<211> LENGTH: 16
<212> TYPE: PRT
<213> ORGANISM: Homo sapiens

<400> SEQUENCE: 12

Cys Ala Ser Ser Arg Ser Gly Ala Gly Ala Gln Glu Thr Gln Tyr Phe
1               5                   10                  15
```